United States Patent
Hirakawa et al.

(10) Patent No.: US 8,368,746 B2
(45) Date of Patent: Feb. 5, 2013

(54) APPARATUS AND METHOD FOR PROCESSING IMAGE INFORMATION CAPTURED OVER TIME AT PLURALITY OF POSITIONS IN SUBJECT BODY

(75) Inventors: Katsumi Hirakawa, Sagamihara (JP); Masanao Hara, Tokyo (JP)

(73) Assignee: Olympus Corporation, Tokyo (JP)

( * ) Notice: Subject to any disclaimer, the term of this patent is extended or adjusted under 35 U.S.C. 154(b) by 1562 days.

(21) Appl. No.: 11/418,534

(22) Filed: May 4, 2006

(65) Prior Publication Data
US 2006/0202998 A1 Sep. 14, 2006

Related U.S. Application Data

(63) Continuation of application No. PCT/JP2004/018170, filed on Dec. 6, 2004.

(30) Foreign Application Priority Data

Dec. 5, 2003 (JP) .................................. 2003-408233
Feb. 4, 2004 (JP) .................................. 2004-028579

(51) Int. Cl.
*A62B 1/04* (2006.01)
*H04N 7/18* (2006.01)
(52) U.S. Cl. .......................................... 348/65; 348/77
(58) Field of Classification Search .................... 348/65, 348/77
See application file for complete search history.

(56) References Cited

U.S. PATENT DOCUMENTS

| 6,346,940 B1 * | 2/2002 | Fukunaga ...................... 345/427 |
| 6,369,812 B1 * | 4/2002 | Iyriboz et al. .................. 345/419 |
| 2002/0009348 A1 | 1/2002 | Fujii et al. |
| 2002/0173718 A1 | 11/2002 | Frisch et al. |
| 2002/0177779 A1 | 11/2002 | Adler et al. |
| 2003/0045790 A1 | 3/2003 | Lewkowicz et al. |
| 2003/0073935 A1 | 4/2003 | Segawa et al. |
| 2003/0195415 A1 | 10/2003 | Iddan |
| 2003/0208107 A1 | 11/2003 | Refael |
| 2005/0075551 A1 * | 4/2005 | Horn et al. ..................... 600/361 |

FOREIGN PATENT DOCUMENTS

| JP | 2003-116781 | 4/2003 |
| JP | 2003-524448 | 8/2003 |
| WO | WO 00/22975 | 4/2000 |

OTHER PUBLICATIONS

Supplementary Partial European Search Report, dated Mar. 11, 2011, in counterpart European Patent Application No. 04819963.

* cited by examiner

*Primary Examiner* — Richard Torrente
(74) *Attorney, Agent, or Firm* — Scully, Scott, Murphy & Presser, P.C.

(57) ABSTRACT

An image captured by successive imaging over time by using a capsule endoscope is correlated with the imaging position and compiled into a database. The left side of a display screen of a monitor device displays a subject internal model, a trajectory path of the capsule endoscope, and a position mark indicating the imaging position. An image corresponding to the position of the position mark is displayed in an image display area on the right side. When a position mark on the trajectory path is designated by a mouse, the corresponding image is displayed. It is also possible to designate a section for which the image corresponding to the position mark is displayed or to designate a position mark where an unusual image is captured.

45 Claims, 15 Drawing Sheets

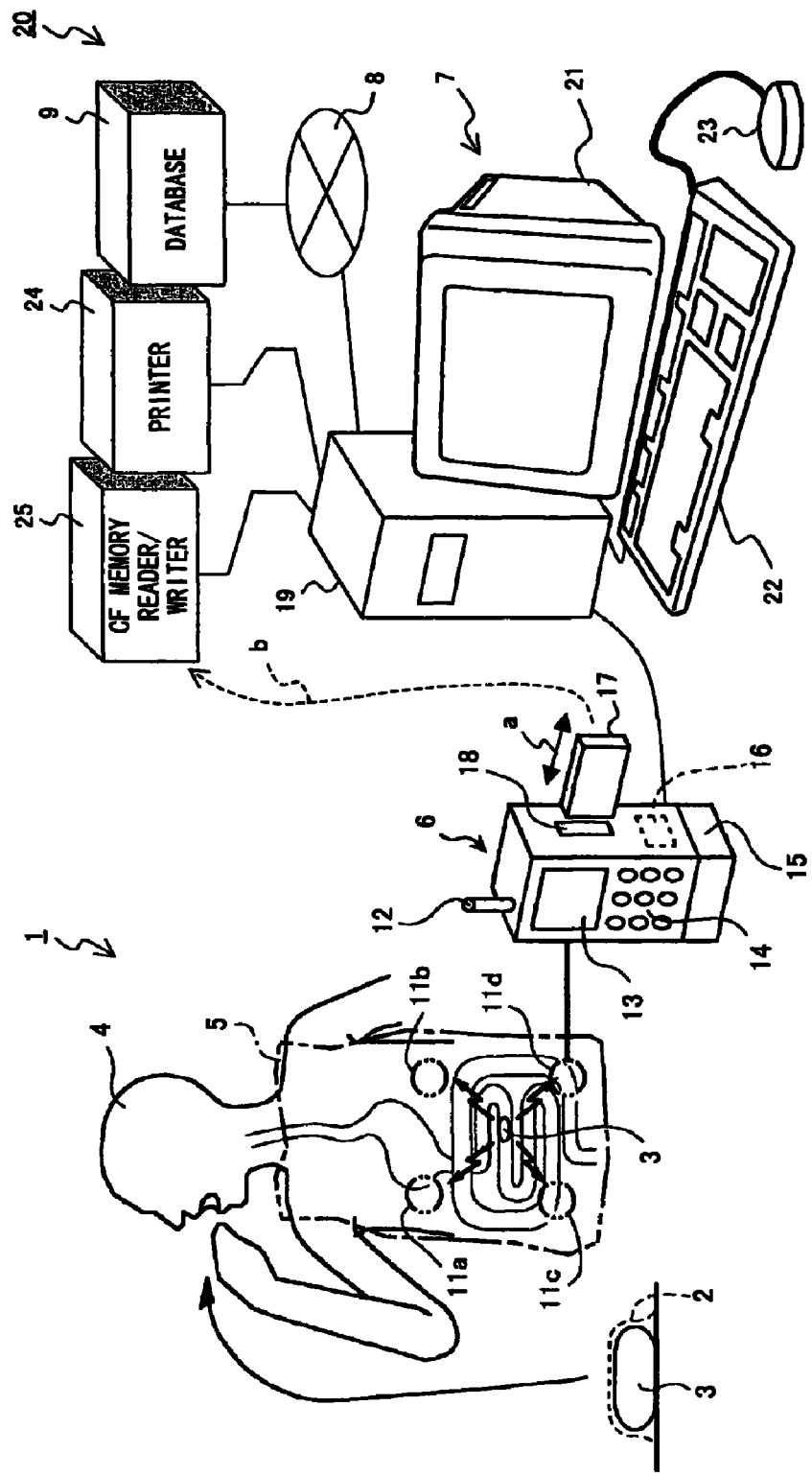
F I G. 1

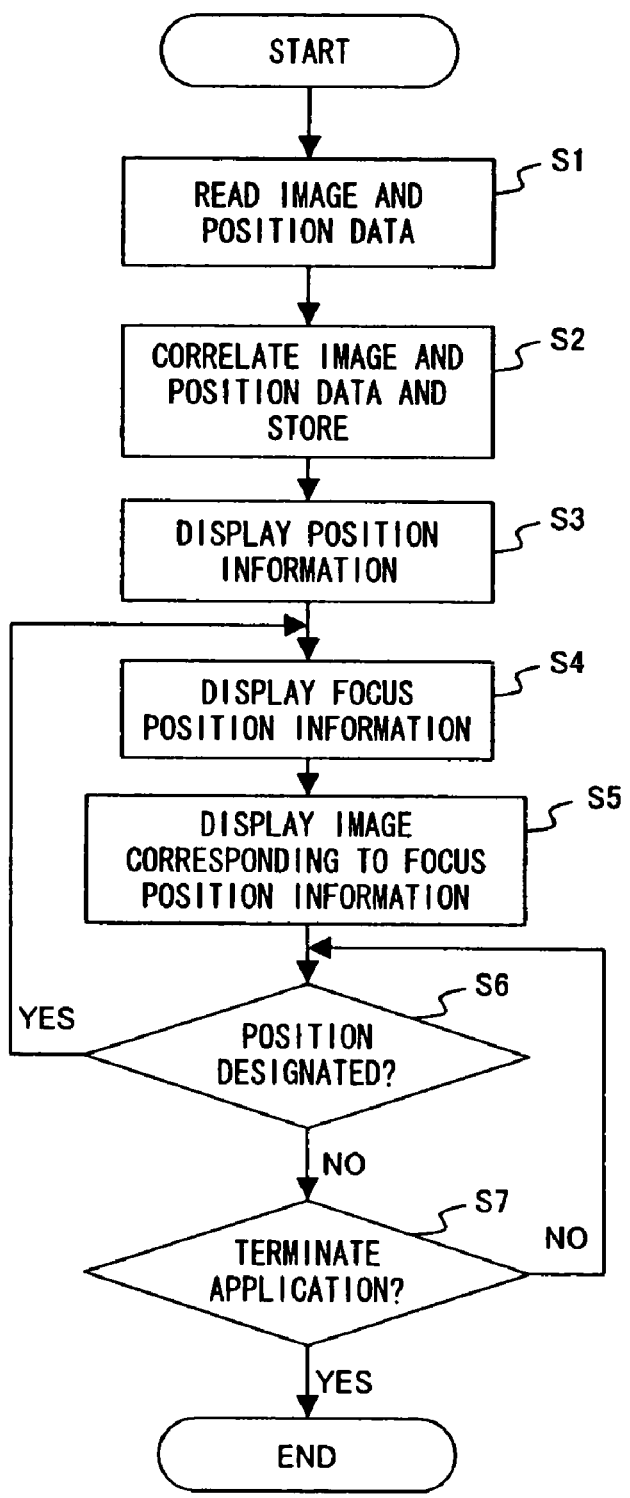
F I G. 3

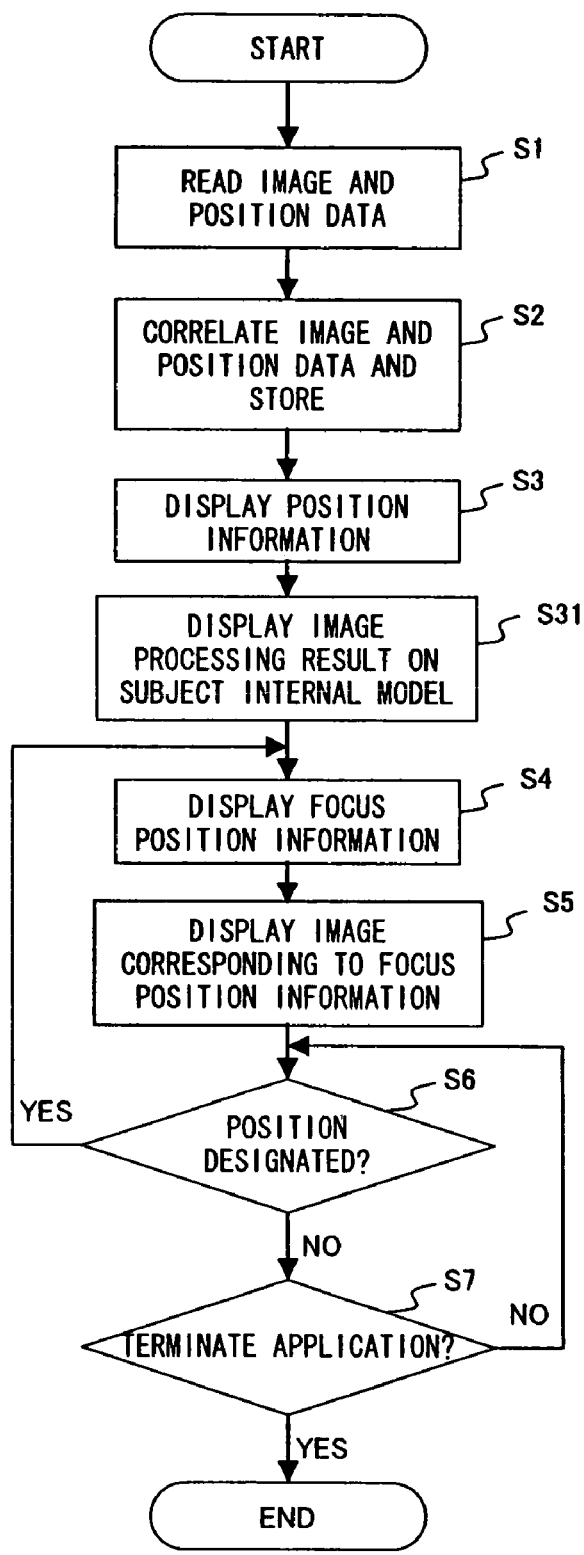
F I G. 6

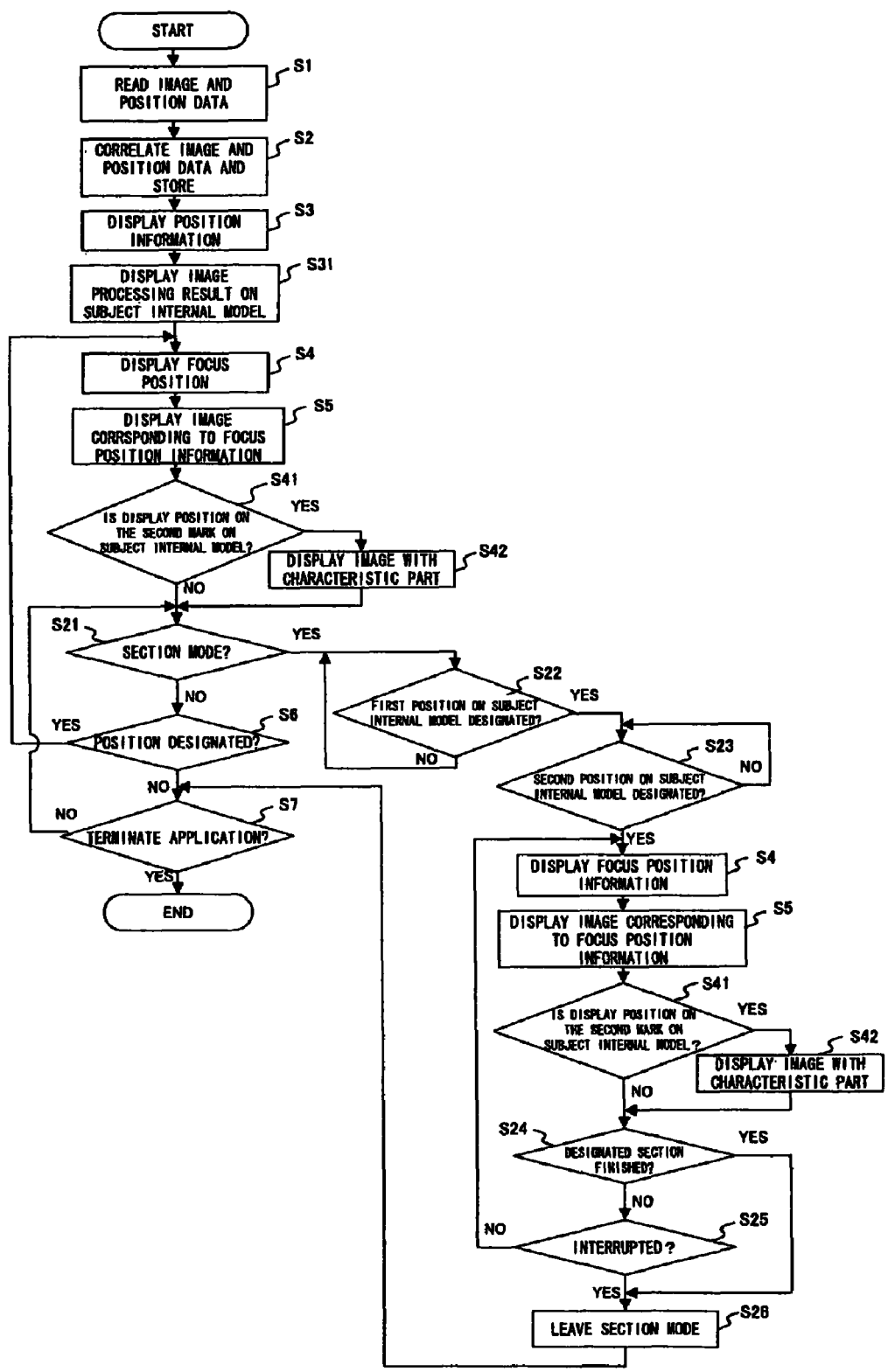
F I G. 9

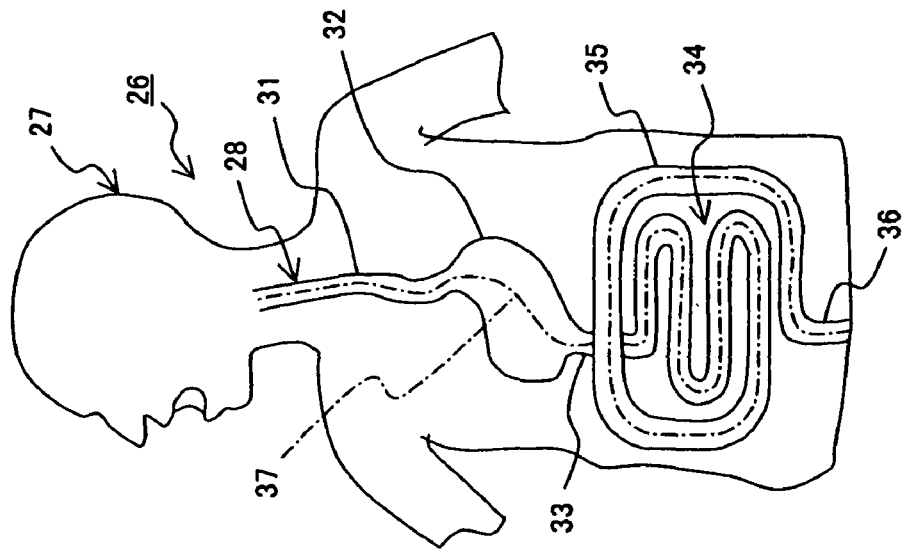
F I G. 10 A
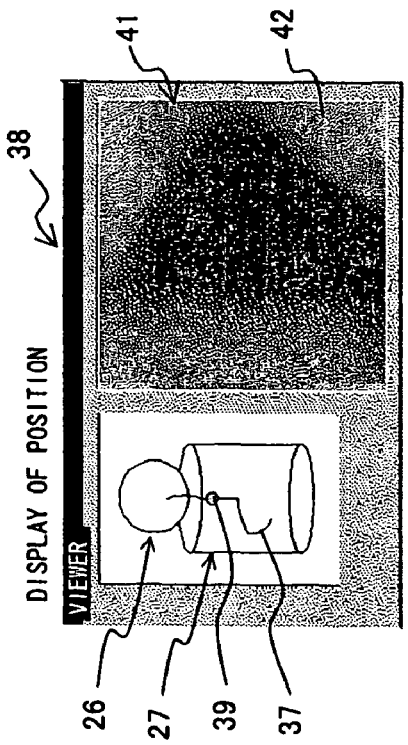
F I G. 10 B
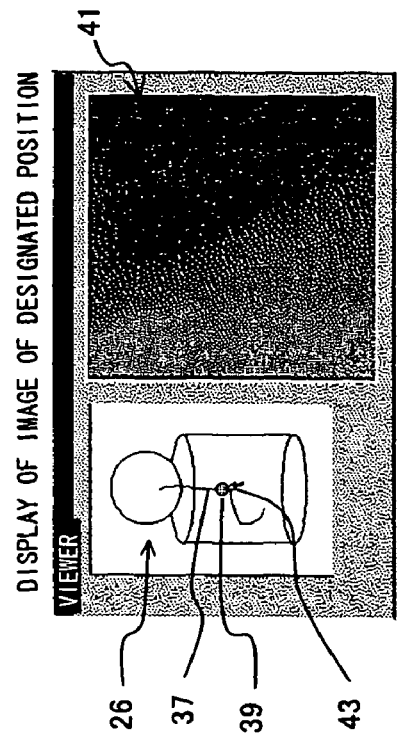
F I G. 10 C

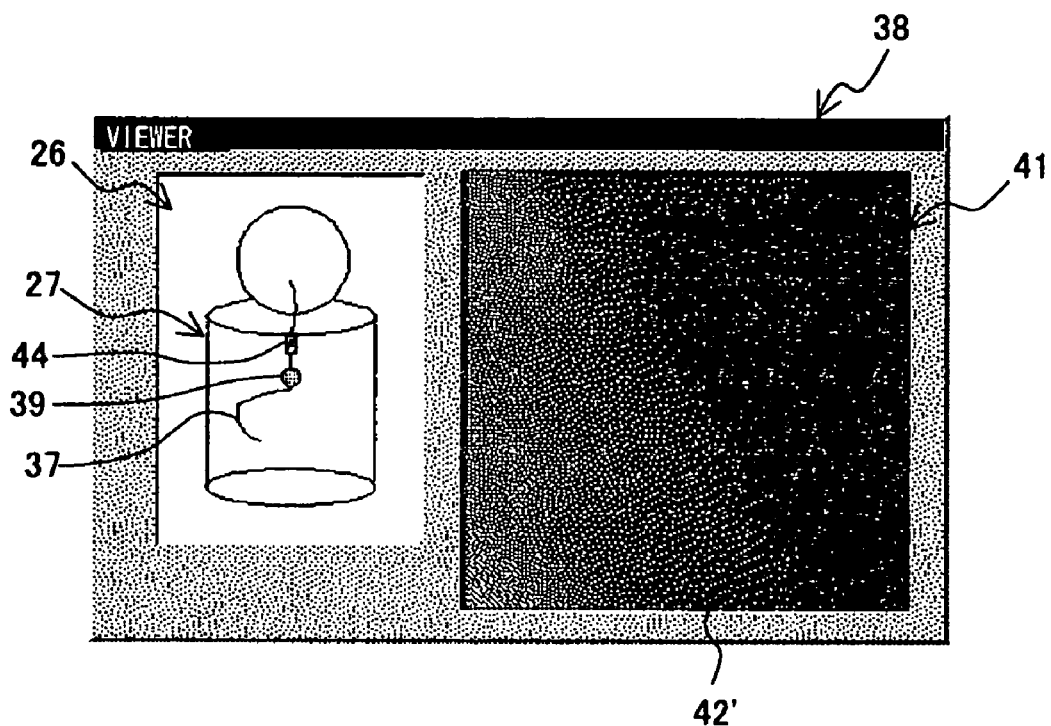
F I G. 1 2 A
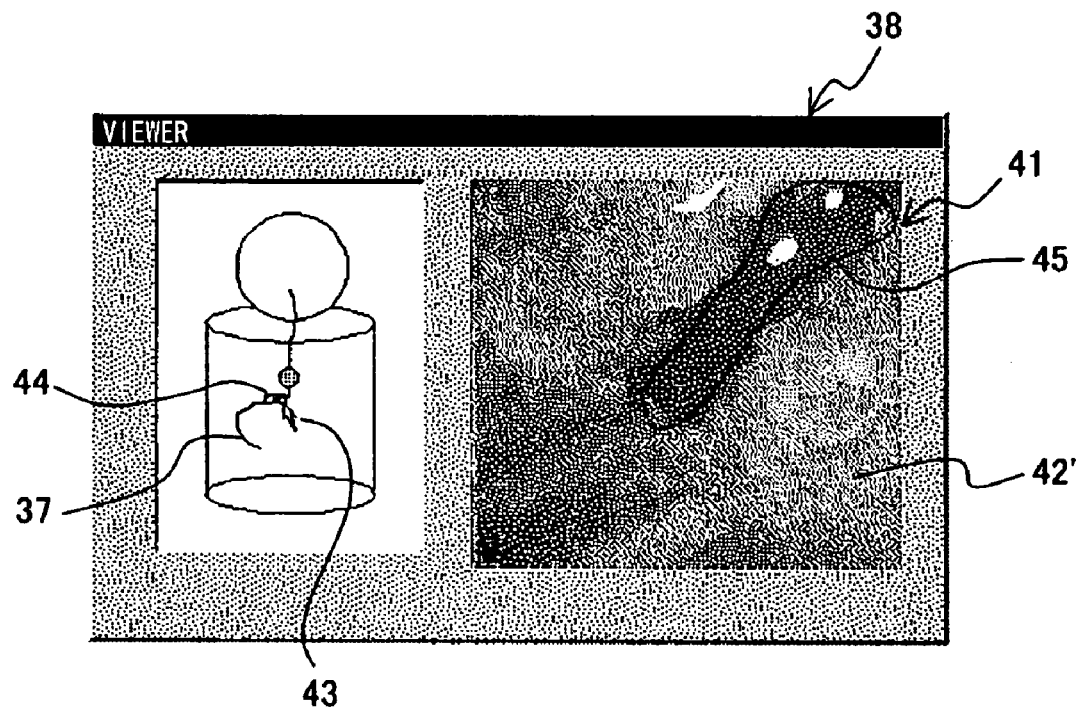
F I G. 1 2 B

APPARATUS AND METHOD FOR PROCESSING IMAGE INFORMATION CAPTURED OVER TIME AT PLURALITY OF POSITIONS IN SUBJECT BODY

CROSS REFERENCE TO RELATED APPLICATIONS

This application is a continuation application of international PCT application No. PCT/JP2004/018170 filed on Dec. 6, 2004.

This application claims benefit of Japanese Applications No. 2003-408233, filed Dec. 5, 2003, and NO. 2004-28579, filed Feb. 4, 2004, the contents of which are incorporated by this reference.

BACKGROUND OF THE INVENTION

1. Field of the Invention

The present invention relates to a technique such as capsule endoscopy, which moves autonomously or heteronomously within the body of a subject and performs display processing of a plurality of information imaged over time, and to a maintenance technique of successively shot image data captured by such an automatic traveling type imaging device.

2. Description of the Related Art

Lesions of luminal organs such as the esophagus and gastrointestinal organs include bleeding, tissue damage, vascular anomalies, Crohn's disease, polyps and so forth, for example. When these lesions develop, most of them cause changes in the intraluminal surface color and the intraluminal surface structure.

A processing unit, suggested in view of this fact, has the features of a transmitter with an imaging function which is released into the luminal organs in search of the presence/absence of a lesion or the cause of a lesion, receiving image data transmitted from the transmitter with an imaging function, analyzing whether or not a calorimetric abnormality is observed by comparison of the received image with at least one reference value, and generating an index of the possibility of a lesion (see Patent Document 1, for example). The device is an endoscope of the type that is swallowed, and thus is called a capsule endoscope.

The capsule endoscope comprises an imaging function and a wireless communication function, and sequentially captures images of organs such as the stomach and intestines, and performs wireless transmission of the captured image data (electronic data representing the images) in series during the observation period, that is from the time it is swallowed by a patient from his/her mouth to the time it is passed out of the human body, for the purpose of an observation or an examination.

The image information transmitted by wireless in the above manner is received by a receiver provided outside the patient's body and is compiled in prescribed memory and later by reading and displaying the information on a display as needed, the information can be of use when a doctor makes a diagnosis or on other occasions.

However, in such a capsule endoscope, unlike conventional endoscopes, because the observation period or examination period is the time period from being swallowed by the patient until being naturally passed out of the body, the observational period and examination period may last for a long time, more than 10 hours for example, and therefore the number of image information acquired by imaging during the period is potentially enormous.

In these circumstances, during the stages of a diagnosis etc., it is not easy to comprehend such a large number of image information in a short period, and it is also not an easy task to locate the image information of a part intended to be focused on, or more specifically image information exclusively of an organ intended to be diagnosed or image information related to an image capturing an ailing part etc. from an enormous number of image information.

In view of the above historical situation, a first object that the present invention aims to achieve is to provide a display processor, a display processing method, and a display processing program for image information, which enables the easy comprehension of a number of image information and the location of image information in which a position intended to be focused on and ailing parts etc. are imaged from a number of image information.

The technique disclosed in the above Patent Document 1 has the central feature of analyzing a calorimetric abnormality and generating an index of the possibility that a lesion is present, and is supposed to be able to display the positions of an image and a capsule (a transmitter with an imaging function and a capsule endoscope) on a single monitor; however, how the positions of the image and the capsule are displayed is not described, and the description lacks an operation of the above processor for displaying the positions of the image and the capsule on a single monitor. Therefore, by the device and method described in the document alone, it is in practice difficult to realize display of the positions of the image and the capsule on a single monitor.

In general, a status of processing is commonly displayed in a progress bar, and in such a progress bar, a progress mark on a horizontal bar moves sequentially from the left to the right (from the bottom to the top in a case of a vertical bar). When the bar progresses to the end, processing is terminated. However, although such a display by a progress bar can indicate time progress or the percentage of processing completed, the location currently being processed of the processed subject cannot be indicated.

Likewise, the technique disclosed in the above Patent Document 1, does not provide any system to indicate the processing status that is the location in the luminal organs of the body, when performing image processing such as extracting a particular image from a number of images.

In view of the above situation, a second object of the present invention is to provide a successive image filing device, a successive image data processing method, and a successive image data processing program, which enables the recording of successive image data captured by an automatic traveling type imaging device in association with focus position information of the automatic traveling type imaging device, and to make the status of the image processing readily visible in the process of image processing, in which the recorded successive image data is extracted according to a certain criterion.

Patent Document 1: US Patent Published Application No. 2002/0177779A1

SUMMARY OF THE INVENTION

A display processor, which is one of the embodiments of the present invention, first, is a display processor of a first invention for causing a display unit to display a plurality of image information acquired by capturing images over time at a plurality of positions in a subject body by an imaging device introduced into the subject body, and is configured so as to comprise an image information acquisition unit for acquiring a plurality of the image information, a position information acquisition unit for acquiring a plurality of position information, correlated with each of a plurality of the image information and relating to each position in the subject body where the imaging device captured images over time, a position information display unit for causing the display unit to display, based on a plurality of the position information, the position where the imaging device captured images over time as a diagram in at least one dimension, a focus position information instruction unit for indicating at least one among a plurality of the position information as focus position information, and an image display unit for causing the display device to display image information correlated with the position information indicated as the focus position information among a plurality of the position information displayed as diagrams.

The display processor of image information is configured so as to further comprise, for example, a position mark display unit for displaying a prescribed mark at a position corresponding to the focus position information in the diagram among a plurality of position information displayed as a diagram by the position information display unit.

The display processor of image information, is also configured so as to further comprise, for example, a storage unit for storing a plurality of image information and a plurality of position information, and the image display unit causes the display unit to display by reading the image information correlated with the position information designated as the focus position information from the storage unit.

The focus position information designation unit is configured so as to further comprise, for example, a designated position input unit for designating arbitrary position information on the diagram as the focus position information among a plurality of position information displayed as the diagram by the position information display unit.

The display processor of image information, also, is configured so as to further comprise a characteristic image detection unit for extracting image information with a designated characteristic part among a plurality of image information, and is configured so that the focus position information designation unit designates position information, relating to the image information with a designated characteristic extracted in the characteristic image detection unit, as the focus position information.

An image information display processing method, which is one of the other embodiments of the present invention, is a display processing method for displaying a plurality of image information acquired by capturing images at a plurality of positions in a body over time on the display screen of a monitor device, and is configured so as to comprise an image information acquisition process for acquiring a plurality of the image information, a position information acquisition process for acquiring a plurality of position information, correlated with each of a plurality of the image information and relating to each position in the subject body where the imaging device captured images over time, a position information display process for causing the display unit to display, based on a plurality of the position information, the position where the imaging device captured images over time as a diagram in at least one dimension, a focus position information instruction process for indicating at least one among a plurality of the position information displayed on a plurality of the position information, and an image display process for causing the display device to display image information correlated with the position information indicated as the focus position information among a plurality of the position information displayed as diagrams.

The display processing method of image information is established, for example, so as to further comprise a position mark display process for displaying a prescribed mark at a position corresponding to the focus position information in the diagram among a plurality of position information displayed as a diagram by the position information display unit.

The display processing method of image information is established so as to further comprise, for example, a storage process for storing a plurality of image information and a plurality of position information, and the image display process causes the display process to display by reading the image information correlated with the position information designated as the focus position information from the storage process.

The focus position information designation process is established so as to further comprise, for example, a designated position input process for designating arbitrary position information on the diagram among a plurality of position information displayed as the diagram by the position information display process.

The display processing method of image information is established so as to further comprise, for example, a characteristic image detection process for extracting image information with a designated characteristic part among a plurality of image information, and is established so that the focus position information designation process designates position information, relating to the image information with a designated characteristic extracted in the characteristic image detection process, as the focus position information.

Recording medium, which is one of the other embodiments of the present invention, is recording media for recording a display processing program for displaying a plurality of image information, acquired by capturing images at a plurality of positions over time in a subject body on a display screen of a monitor device by computer, and is configured so that the display processing program causes the computer to perform image information acquisition processing for acquiring a plurality of the image information, position information acquisition processing for acquiring a plurality of position information, correlated with each of a plurality of the image information and relating to each position at which an image was captured over time in the subject body, position information display processing for causing display, based on a plurality of the position information, positions at which the images were captured over time in the subject body as a diagram in at least one dimension, focus position information instruction processing for indicating at least one among a plurality of the position information as focus position information, and image display processing for causing display of an image information correlated with the position information indicated as the focus position information among a plurality of the position information displayed as diagrams.

The display program of image information is configured so as to further cause the computer to perform, for example, position mark processing for causing display of a prescribed mark at a position corresponding to the focus position information of the diagram among a plurality of position information displayed by the position information display processing as a diagram.

The display processing program of image information further comprises storage processing for storing a plurality of image information and a plurality of position information, and is configured so that the image display processing causes the computer to perform processing to read out and display the image information stored by executing the storage processing and correlating it with the position information designated as the focus position information.

The focus position information designation processing is configured so as to further comprise, for example, designated position input processing for designating arbitrary position information in the diagram as the focus position information among a plurality of the position information displayed as the diagram by the position information display processing.

The display processing program of image information further comprises, for example, characteristic image detection processing for extracting image information with a designated characteristic part among a plurality of image information, and the focus position information designation processing is configured so as to cause the computer to further perform the designation of the position information correlated with the image information with the designated characteristic extracted by the characteristic image detection processing as the focus position information.

An image filing device for a capsule endoscope, which is one of additional embodiments of the present invention, is an image filing device for a capsule endoscope for processing successive image data captured in succession by a capsule endoscope moving inside a subject body at a prescribed time interval, and is configured so as to comprise a focus position information acquisition unit for acquiring an arbitrary position from one or more of position information relating to the position inside the subject body where the successive image data is acquired as focus position information, an image information acquisition unit for acquiring image information corresponding to the position designated as the focus position information from the successive image data; a position display unit for displaying one or more of position information in the subject body as a diagram in at least one dimension, an image information processing unit for applying prescribed processing to the image information acquired by the image information acquisition unit, and a progress information display unit for superimposing and displaying the position of the focus position information acquired by the focus position information acquisition unit on the diagram displayed by the position display unit, and for indicating the progress of processing by the image information processing unit by the display change of the diagram of the focus position information.

The position display unit is configured, for example, so as to display a trajectory path of the capsule endoscope inside the luminal organs in the body while displaying the average locations of the internal organs as a background of the trajectory path.

The progress information display unit is configured so as to superimpose and display the display indicating the progress and the processing result by the image information processing unit on the display of the position display unit.

The image filing device for a capsule endoscope id configured so as to comprise an image information display unit for displaying progress of processing of the image information processing unit and image information corresponding to the processing of the image information processing unit.

In this case, the image information display unit is configured so as to display the processing result of the image information processing unit, for example, in such a way that the display is superimposed on the display of the image information, and the image information display unit is configured so as to update and display the image information at a prescribed time interval.

The image filing device for a capsule endoscope comprises an instruction input unit for receiving an instruction from a device-operator, and the image information processing unit is configured so as to perform control of the image information processing based on the input result of the instruction input unit.

In such a case, the control of the image information processing in the image information processing unit based on the input result of the instruction input unit is, for example, the end of the processing, the suspension of the processing, the resumption of the processing, or the change of image information to be processed.

The processing content in the above image filing device for a capsule endoscope becomes the image filing processing method for a capsule endoscope, which is one of the other embodiments of the present invention, and also the recording medium in which the program for executing the above processing is recorded, is recording media, which is one of the additional embodiments of the present invention.

BRIEF DESCRIPTION OF THE DRAWINGS

The present invention will be more apparent from the following detailed description when the accompanying drawings are referenced.

FIG. 1 is a diagram showing an overview of a configuration of a capsule endoscope image filing system relating to the present invention;

FIG. 3 is a flowchart explaining operation of the image processing of the capsule endoscope image filing system relating to the first embodiment of the present invention;

FIG. 6 is a flowchart explaining the operation of the image processing of the capsule endoscope image filing system relating to the third embodiment of the present invention;

FIG. 9 is a flowchart explaining the operation of the image processing of the capsule endoscope image filing system relating to the fifth embodiment of the present invention;

FIG. 10A is a diagram showing a second example of the luminal organ model of the subject individual displayed on the display screen of the capsule endoscope image filing system;

FIG. 10B is a diagram showing a fourth example of the subject internal model and the image of the subject individual displayed on one display screen of the monitor device of the workstation in the capsule endoscope image filing system of the present invention;

FIG. 10C is a diagram showing a fifth example of the subject internal model and the image of the subject individual displayed on one display screen of the monitor device of the workstation in the capsule endoscope image filing system of the present invention;

FIG. 12A is a diagram showing a first example of a luminal organ model and the image of the subject individual displayed on one display screen of the monitor device of the workstation of the capsule endoscope image filing system relating to the seventh through the tenth embodiments of the present invention;

FIG. 12B is a diagram showing a second example of a luminal organ model and the image of the subject individual displayed on one display screen of the monitor device of the workstation of the capsule endoscope image filing system relating to the seventh through the ninth embodiments of the present invention;

DESCRIPTION OF THE PREFERRED EMBODIMENTS

Figure 2A:
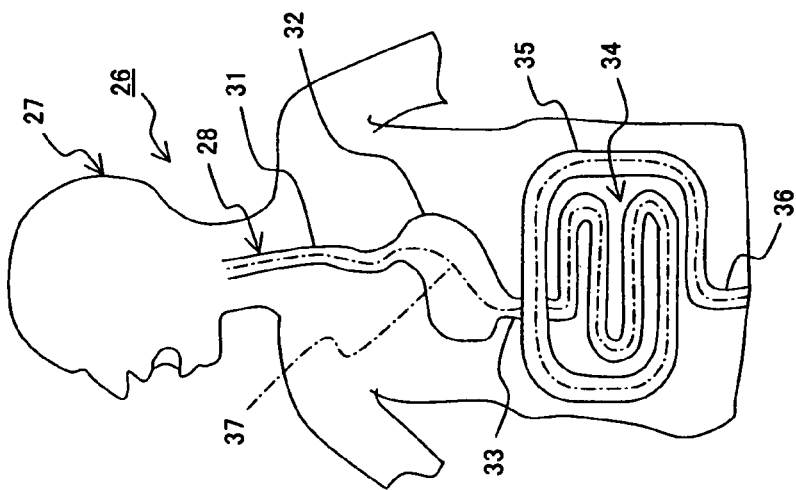
FIG. 2A is a diagram showing a first example of the subject internal model of the subject individual displayed on a display screen of the capsule endoscope image filing system.

In the following description, details of the embodiments for carrying out the present invention are set forth with reference to the drawings.

In the following explanation, the above subject is a subject individual 4 for example, the above imaging device is a capsule endoscope 3 for example, the above display unit is a monitor device 21 for example, the above display processor is a workstation 7 for example, the above image information is image data for example, the above image information capture unit is an antenna 11 for example, the above position information is a trajectory path 37 and position data for example, the position information acquisition unit is the antenna 11 for acquiring the position data for establishment of the trajectory path 37 for example, displayed by the monitor device, the above position information display unit is, for example, the monitor device 21 and the subject body model 27, the trajectory path 37, position mark 39, the second position mark 44 and so forth, the above focus position information is, for example, particular position information in the above position information, the above focus position information instruction unit is the position mark 39 for example, the above image display unit and the position mark display unit for example is the monitor device 21, the above storage unit is a database 9 for example, the above diagram is the subject internal model 26, the above designated position input unit is a keyboard 22 and a mouse 23 for example, and the above characteristic image detection unit is the workstation 7, for example.

In the following explanation of the embodiment of the present invention, the above subject in the image filing device for the capsule endoscope comprises a subject individual 4 etc., the successive image data etc. of the capsule endoscope 3, for example, comprises image data etc., the position information comprises image position data of the image data. The trajectory path 37 of the capsule endoscope 3 is displayed as a diagram in one or more dimensions. The focus position information is one of position information, which is image position data of the image data. The focus position acquisition unit comprises, for example, the antenna 11 and the receiver 6 etc., the image information comprises, for example, image data, the image information capture unit comprises, for example, the antenna 11, the receiver 6 and the workstation 7 etc., the diagram in one or more dimensions comprises, for example, a luminal organ model 26 etc., the position display unit comprises, for example, a display screen 38 etc. of the monitor device 21, the image information processing unit comprises, for example, a main device 19 etc. of the workstation 7, the position of the focus position information comprises, for example, the position mark 39 etc., the display indicating the status of processing comprises, for example, the position mark 39 and the trajectory path 37 etc., the progress information display unit comprises, for example, the display screen 38 etc. of the monitor device 21, the image information display unit comprises, for example, image display area 41 etc. of the display screen 38 of the monitor device 21, the processing result comprises, for example, an unusual image 42' etc., the image information corresponding to the processing comprises, for example, the characteristics detection target position 45 etc., the device operator includes, for example, a doctor or a nurse etc., and the instruction input unit comprises, for example, the display screen 38, the keyboard 22, and the mouse 23 etc. of the monitor device 21 of the workstation 7. The control of the image information processing is the processing shown in the flowcharts etc. of FIG. 3, FIG. 5-FIG. 9, FIG. 11, and FIG. 13-FIG. 15, for example.

FIG. 1 is a diagram showing an overview of a configuration of a capsule endoscope system and a capsule endoscope image filing system comprised in the above system, relating to the present invention. As shown in FIG. 1, a capsule endoscope system 1 of the present example comprises a capsule endoscope comprised in a package 2, a patient or a subject individual 4, who is to swallow the capsule endoscope 3 extracted from the package 2, a jacket 6 for the subject individual 4 to wear, and a receiver 6, which can be attached to/detached from the jacket 5.

A capsule endoscope image filing system 20 comprises a workstation 7 for performing processing such as storing or editing of the image data received from the above receiver 6, and database 9 connected to the workstation 7 over a network 8. The database 9 can be incorporated into the workstation 7.

In the above capsule endoscope 3, an imaging unit, a wireless unit and power source are configured. The capsule endoscope 3, wirelessly transmits image data, which was captured in the esophagus, the stomach, the small intestine, the large intestine and other locations by serially imaging over time under the control of the imaging unit, from the wireless unit to external entities as radio waves during the period between being swallowed orally, for an observation or an examination, until being passed out of the body of the subject individual 4.

The jacket 5 to be worn by the subject individual 4 comprises a plurality (four in the example of FIG. 1) of antennas 11 (11a, 11b, 11c, 11d) for picking up the transmitted radio waves of the image data transmitted from the wireless unit of the capsule endoscope 3. These antennas 11 are configured so as to perform wired or wireless communication with the receiver 6. The number of antennas 11 is not particularly limited to four, but an appropriate number should be provided accordingly. That is, the number of installed antennas can be any number, as long as the transmitted radio waves can be received sufficiently well according to the position as the capsule endoscope 3 moves.

The receiver 6 comprises an antenna 12 used in receiving image data by radio waves from the jacket 5 over the antenna 11, a display unit 13 for indicating information necessary for the observation or the examination, and an input unit 14 for inputting information required for the observation or the examination.

In the bottom of the receiver 6, a power source unit 15 is configured so as to be able to supply power when the receiver is being carried. The power source unit 15 comprises a dry-cell battery, a Li (Lithium)-ion secondary battery, or Ni (Nickel)-hydride battery etc. (Other types of battery can also be used).

In addition, in the receiver 6, a signal processing/control unit 16 for performing processing necessary for the observation or the examination is configured, and an attachment unit 18 for attaching CF (Compact Flash (Trademark)) memory 17 for storing the received image data, so as to be removable as indicated by the bidirectional arrow a.

The workstation 7 comprises the main device 19, the monitor device 21 connected to the main device 19, the keyboard 22, the mouse 23 and so forth, in addition, the main device 19 comprises various types of interface, not specifically shown in the drawings, other than an interface for connecting to the network 8 mentioned above, a printer 24 and a CF memory reader/writer 25 in addition to the above receiver 6 via these interfaces. The workstation 7 comprises an image processing function for diagnosing etc. by a doctor or a nurse displaying the images of the digestive tract of the subject individual 4, captured by the capsule endoscope 3 on the monitor device 21.

The doctor or the nurse, while performing an input operation to a man-machine interface displayed on the monitor device 21 of the workstation 7 using the keyboard 22 and the mouse 23, can issue an instruction to capture the image data, transmitted from the capsule endoscope 3 and received by the receiver 6, of the luminal organs of the subject individual 4 from the receiver 6.

The capture of the image data from the receiver 6 is also possible by the direct capture from the receiver 6 by a cable, or the image data can also be captured from the CF memory 17 by attaching the CF memory 17 to the CF memory reader/writer 25 as indicated by an arrow b in FIG. 1.

Furthermore, the doctor or the nurse can send such instructions as the instruction to store image data captured from the receiver 6 in the above manner to the database 9, an instruction to perform image display relating to image data, explained later, on the display screen of the monitor device 21 after calling up the image data stored in the database 9, an instruction to record the result of the diagnosis etc., based on the observation of the image, to the database 9, and an instruction to print medical records and etc. to the printer 24.

The workstation 7 comprises a computer of a standard configuration, that is, a computer comprising a central processing unit (CPU) for controlling each component by executing control programs, ROM, RAM, a magnetic-storage device and so forth, and also comprising a storage unit used as a storage area for a control program for causing the CPU to control each component and as a work area for various data when the CPU executes the control program, an input unit, by which various data corresponding to the user operations is acquired, an output unit for informing a user of various information by presenting the data on a display etc., and an I/F unit for providing an interface function for data transmission to/reception from the other equipment. In order for the computer with such a standard configuration perform the processing shown in the flowcharts etc. of FIG. 3, FIG. 5-FIG. 9, FIG. 11, and FIG. 13-FIG. 15 as explained later, a control program, causing the computer to perform the processing, the procedure of which is shown in a flowchart in each drawing, is created and is recorded on recording media 100, which is readable by a computer, and the control program is executed after the CPU of the computer reads out the control program from the recording media 100.

As the recording media 100, from which the recorded control program is readable by a computer, for example, portable recording media etc. such as RAM or ROM configured as built-in or external auxiliary equipment of the computer, memory such as a hard disk device, FD (Flexible Disk), MO (Magneto-optical disk), CD-ROM, and DVD-ROM can be used.

The recording media 100 can be a storage device that is connected to a computer via a line, functions as a program server, and is comprised in another computer. In such a case, the control program can be executed by a process of the transmission signal, acquired by modulating a carrier wave with a data signal representing the control program, being transmitted from the program server via a communication line, which is the transmission media, and the control program is regenerated by demodulating the received transmission signal in the computer.

It is obvious that although the explanation of the embodiments of the present invention focuses on a capsule endoscope system and a capsule endoscope image filing system, the present invention is not limited to such systems.

<First Embodiment>

Figure 2B:
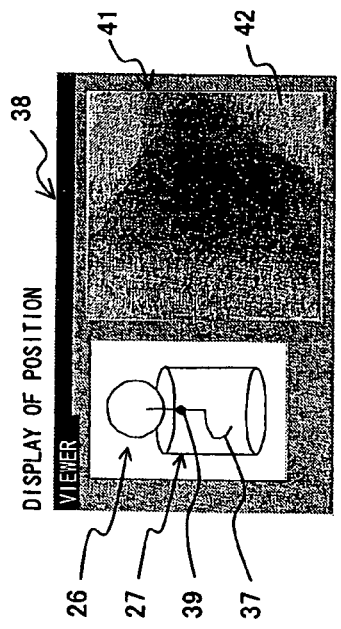
FIG. 2B is a diagram showing the first example of a subject internal model and the image of a subject individual displayed on the same display screen of a monitor device of a workstation of the capsule endoscope image filing system of the present invention.
Figure 2C:
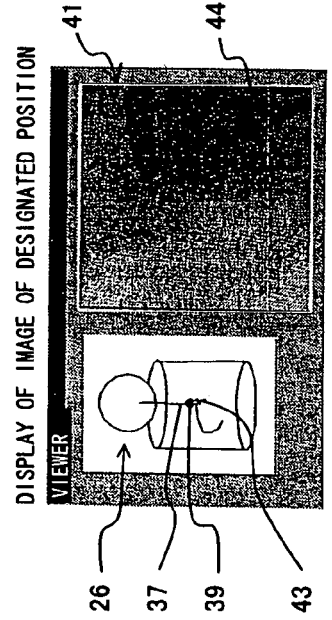
FIG. 2C is a diagram showing a second example of a subject internal model and the image of a subject individual displayed on the same display screen of a monitor device of a workstation of the capsule endoscope image filing system of the present invention.
Figure 2D:
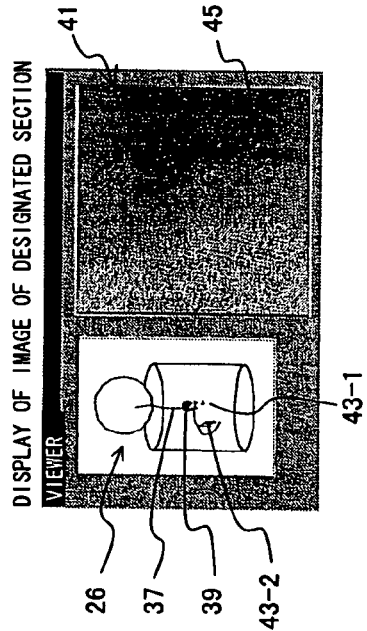
FIG. 2D is a diagram showing a third example of a subject internal model and the image of a subject individual displayed on one display screen of a monitor device of a workstation of the capsule endoscope image filing system of the present invention.

FIG. 2A, FIG. 2B, FIG. 2C and FIG. 2D are diagrams of the subject internal model 26 of the subject individual 4 and examples of an image 42, both of which are displayed on the same display screen 38 of the monitor device 21 of the workstation in the capsule endoscope image filing system relating to the present invention in terms of the first embodiment. FIG. 2A is a diagram showing the subject internal model of the subject individual 4 displayed on a display screen of the monitor device 21 and FIG. 2B, FIG. 2C and FIG. 2D are diagrams showing examples of images displayed on the same display screen of the monitor device 21 as the subject internal model. FIG. 2B, FIG. 2C and FIG. 2D simplify the subject internal model shown in FIG. 2A for the convenience of the explanation.

As shown in FIG. 2A, both the subject body model 27 of the subject individual 4 and a digestive organ model 28 are indicated as a frame format of a two-dimensional diagram as a subject internal model 26 of the subject individual 4. The digestive organ model 28 comprises digestive organs such as an esophagus 31, a stomach 32, a duodenum 33, a small intestine 34, a large intestine 35, and a rectum 36 indicated in a frame format. In the digestive organ model 28, a trajectory path 37 is displayed as position information relating to the positions where the capsule endoscope 3 passed and captured images. Here, the above diagram is not limited to two dimensions.

As shown in FIG. 2B, FIG. 2C and FIG. 2D, on the display screen 38 of the monitor device 21, the above subject internal model 26 is displayed on the left, and the position mark 39 is superimposed and indicated on the trajectory path 37 of the capsule endoscope 3 as a prescribed mark for indicating the position relevant to the imaging positions in the subject body. In an image display area 41 to the right of the subject internal model 26, an image 42 captured at a position in the subject body relevant to the position on the trajectory path 37 corresponding to the position mark 39 or specifically to the processing explained later is displayed.

FIG. 2C shows an example where a pointing arrow 43 is displayed by operation of the mouse 23, which serves as the designated position input unit for pointing to the position mark 39, and FIG. 2D shows an example where two (a first and a second) pointing arrows 43 (43-1 and 43-2), designating a section by the mouse 23 operation, are displayed.

Next, an explanation of a processing operation in the first embodiment in an image processing of the above capsule endoscope image filing system is given.

FIG. 3 is a flowchart explaining an operation of the image processing in the first embodiment. The image processing is processing performed by a controller (hereinafter referred to merely as a CPU) incorporated into the main device 19 based on the instruction input from the key board 22 or the mouse 23 of the workstation 7 shown in FIG. 1 by a doctor or a nurse.

The following operation is performed preceding the above processing. That is, the capsule endoscope 3 is extracted from the package 2 by the subject individual 4, and the power switch installed in the capsule endoscope 3 is turned on. Images of the inside of the digestive organs of the subject individual 4 are successively captured by the imaging unit of the capsule endoscope 3, and a plurality of image data successive in time are acquired during the time period from the capsule endoscope 3 being swallowed by the subject individual 4 until being passed out of the body, after moving by the peristaltic motion of the digestive organs.

The captured image data is transmitted from the wireless unit of the capsule endoscope 3, carried by a radio signal, the signal is received by the antennas 11 (11a, 11b, 11c and 11d) of the jacket 5. The received signal is transferred to the receiver 6.

The receiver 6 performs reception from each antenna 11 in rotation by switching and generates one frame of signal in sequence, pairing the radio intensity of the image signal and the signal content (image data) of the image signal. In other words, if there are four antennas for one image data, four frames of signals are generated. The generated four frames of signals are stored in the CF memory 17 in series. The processing on the receiver 6 side is repeated for every image capture during the image capture by the capsule endoscope 3.

In FIG. 3, the CPU first reads in the image data and position data (S1).

In this processing, the CPU reads out signals, recorded to the CF memory 17, four frames at a time directly from the receiver 6 by a cable or from the CF memory 17 attached to the CF memory reader/writer 25 after being extracted from the receiver 6. The image data is read out from the four frames of received signal, the transmission position of the radio containing the above image data is calculated from the signal strength at each antenna and the position data relating to the calculated capture position is acquired. At this point, it is also possible to consider the antenna with the highest signal strength of received signal as the source of position data without calculating the transmission position.

Next, the CPU stores the acquired image data and position data after correlating them to each other (S2).

This processing is for registering a pair of mutually related image data and position data as a record in the database 9.

Next, the CPU displays position information (S3).

This processing is for displaying position information corresponding to the position in the subject body, where the capsule endoscope 3 passes through in the subject body, or along the trajectory path 37, from the position data acquired in processing S1 on the digestive organ model 28 of the subject internal model 26 shown in FIG. 2A, FIG. 2B, FIG. 2C and FIG. 2D on the display screen of the monitor device 21 of the workstation 7. That is, the changes in the position information with time indicate the trajectory path 37 of the capsule endoscope 3 in the subject internal model 26.

Following the above step, the CPU displays focus position information (S4).

This processing is for displaying the position mark 39 (see FIG. 2B, FIG. 2C and FIG. 2D) representing that it is a part to be focused on when diagnosed by a doctor or a nurse, that is the focus position information, superimposed on the position information on the display screen of the above monitor device 21, that is, on the display of trajectory path 37. In the initial setting of the processing, the position mark 39 is displayed at the position on the display of the trajectory path 37 indicating position information at the first point after the capsule endoscope started image capture.

The CPU, next, displays the image corresponding to the focus position information (S5).

In this processing, the CPU also reads out image data paired with the position data corresponding to the position information at the position on the trajectory path 37 designated as the above focus position information from the database 9 as data within one record, and based on the one record of data, as shown in FIG. 2B for example, the image 42, acquired from image data corresponding to the position on the trajectory path 37 with the display of the position mark 39, is displayed in the image display area 41, to the right of the display screen 38.

The CPU, next, determines whether a new focus position is designated or not (S6).

This processing is to determine whether or not an intended position to be focused on for diagnosis etc. is designated by the pointing arrow 43 as shown in FIG. 2C, by the operation of the mouse 23 of the workstation 7 by a doctor or a nurse on the trajectory path 37 displayed on the currently displayed subject internal model 26.

If the position is not designated by the pointing arrow 43 (S6: Yes), the process returns to the processing S4, and performs processing S4. That is, a position mark 39 indicating that it is designated as focus position information is superimposed and displayed on the position on the trajectory path 37 to which the position to be focused on is designated by the pointing arrow 43.

In this processing, the CPU searches in the database 9, reads out a record, comprising the position data corresponding to the position on the trajectory path 37 on which the focus position is designated by the pointing arrow 43, from the data base 9, and the position mark 39 is superimposed and displayed, as shown in FIG. 2C, at the position on the trajectory path 37 that the focus position information indicates, that is at the position on the trajectory path 37 designated by the pointing arrow 43.

Then, the following processing S5 and the processing S6 are repeated.

If the position is not designated by the pointing arrow 43 in the above processing S6 (S6: No), whether the application is terminated or not is determined (S7), when the application is terminated (S7: Yes), the processing is also terminated; however, the application is not terminated (S7: No), the process returns to the processing S6 and the determination processing of the processing S6 is repeated.

In the above processing in which the position is designated by a doctor or a nurse, for example, the position mark is displayed on the trajectory path 37 when the doctor or the nurse points to any position on the trajectory path 37 by the pointing arrow 43 and left-clicks the mouse 23.

Whether the image corresponding to the position mark 39 displayed on the trajectory path 37 should be immediately and automatically displayed or it should be displayed by left-clicking the mouse 23 once again can be determined by setting the processing mode in advance, before the processing starts.

The processing to terminate the above application can be executed by, for example, preparing menu items not shown on the display screen 38 and by selecting the "end" item on the menu items with the mouse 23.

By so doing, when the doctor or the nurse, looking at the display screen on the monitor device 21 of the workstation 7, designates any intended position on the trajectory path 37 of the subject internal model 26 by moving the pointing arrow 43 by operation of the mouse 23, the position mark 39 is superimposed and displayed on the designated position, and the image corresponding to the position is displayed in the area to the left of the same display screen.

<Second-Fifth Embodiments>

FIG. 4A, FIG. 4B, FIG. 4C and FIG. 4D are diagrams showing examples of the subject internal model 26 and the image 42 of the subject individual 46 displayed on the same display screen of the monitor device 21 of the workstation 7 in the capsule endoscope image filing system relating to the second-fifth embodiments of the present invention.

Figure 4A:
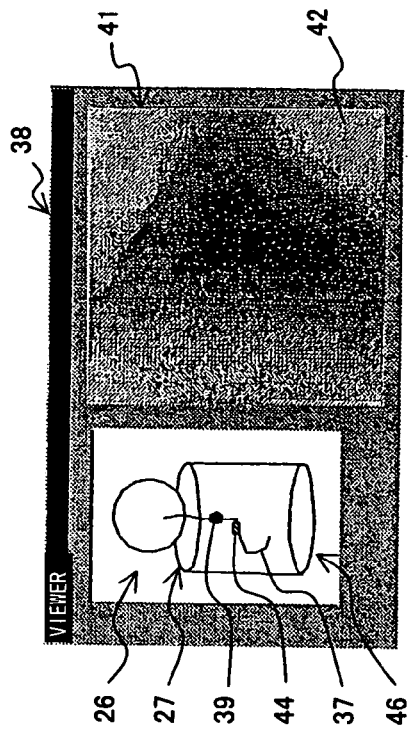
FIG. 4A is a diagram showing a first example of a digestive organ model and the image of the subject individual displayed on one display screen of the monitor device of the workstation of the capsule endoscope image filing system relating to the second through the fifth embodiments of the present invention.

FIG. 4A is, when an unusual image comprising a particular characteristic part (for example, parts indicating bleeding or a polyp) indicating a symptom designated by a doctor or a nurse, is present, by instructing and inputting so as to display the unusual image, image data of the unusual image comprising the prescribed characteristic part is searched for and extracted from the database 9, and at the position on the trajectory path 37 corresponding to the position in the subject body in which the extracted image data is captured, the second position mark 44 is displayed as an image processing result indicating the position of data correlated with the image data comprising a prescribed characteristic part.

The image 42 displayed in the image display area 41 on the right is the original image displayed without any modification.

The second position mark 44 is displayed only in one position in FIG. 4A; however, in the actual display, the second position mark 44 is displayed at the positions on the trajectory path 37 where all images of the image data extracted by the above search are captured.

Figure 4B:
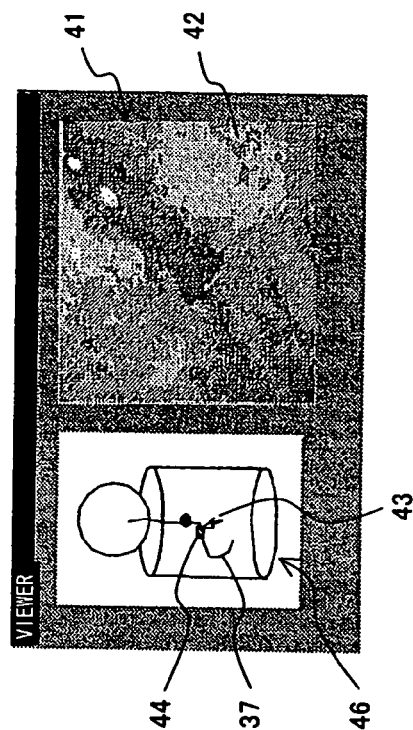
FIG. 4B is a diagram showing a second example of a digestive organ model and the image of the subject individual displayed on one display screen of the monitor device of the workstation of the capsule endoscope image filing system relating to the second through the fifth embodiments of the present invention.

Next, FIG. 4B is an example where the second position mark 44 at a position among the second position marks 44 of all the image data including the designated unusual image displayed on the trajectory path 37 is designated by the pointing arrow 43, and the image 42, based on the image data corresponding to the position where the designated second position mark 44 is displayed, (the position on the display of the trajectory path 37, the same applies to the following description), is displayed in the image display area 41 on the right side.

It is obvious that although FIG. 4B indicates the second position mark 44 at only one position, it is not necessarily limited to one position.

Figure 4C:
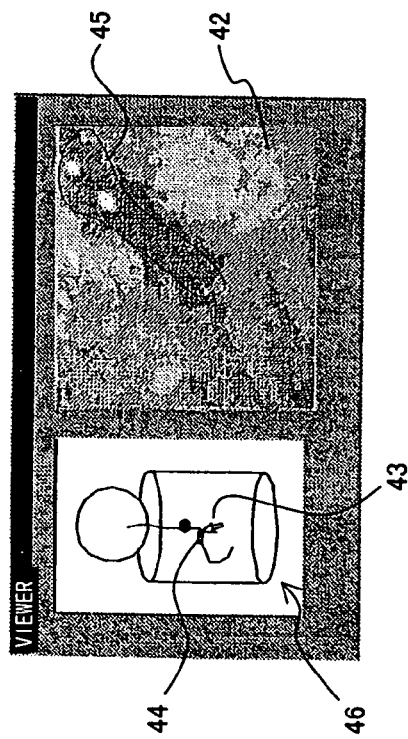
FIG. 4C is a diagram showing a third example of a digestive organ model and the image of the subject individual displayed on one display screen of the monitor device of the workstation of the capsule endoscope image filing system relating to the second through the fifth embodiments of the present invention.

FIG. 4C is an example where the characteristic part 45, which caused extraction of the image 42 from the database 9, is displayed, superimposed on the image 42, which corresponds to the designated second position mark 44 and is displayed in the image display area 41 on the right side.

Figure 4D:
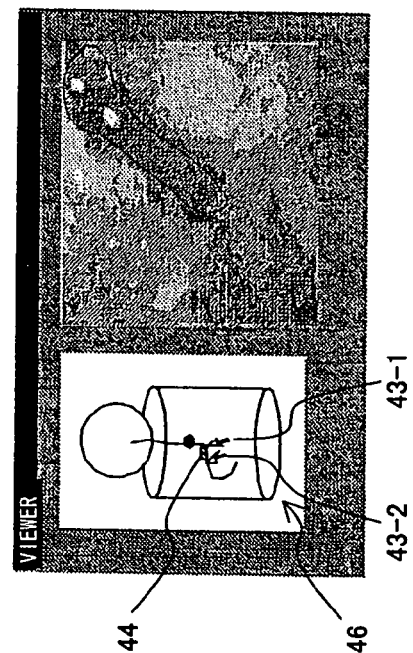
FIG. 4D is a diagram showing a fourth example of a digestive organ model and the image of the subject individual displayed on one display screen of the monitor device of the workstation of the capsule endoscope image filing system relating to the second through the fifth embodiments of the present invention.

FIG. 4D shows an example (referred to as a section mode) displaying two pointing arrows 43 (43-1 and 43-2) for pointing at the first and second marks designating an arbitrary section among any of the above second position marks 44. Here, the section refers to an interval between position information corresponding to each of the two different positions on the display of the trajectory path 37.

In such a case, also, on the display of the display screen 38 of the monitor device 21 in FIG. 4A, FIG. 4B, FIG. 4C and FIG. 4D, a task menu with items such as "Next", "Back", "Designate section" and "End", not shown in the drawings in particular, is displayed in the pull-down menu in the menu button shown in the task bar. It is, of course, not limited to the menu display but it is also possible to have buttons of "Next", "Back", "Designate section" and "End" displayed at all times in an appropriate display area of the display screen.

Following the above process, the processing operation of the image processing in the capsule endoscope image filing system in the second embodiment is explained.

Figure 5:
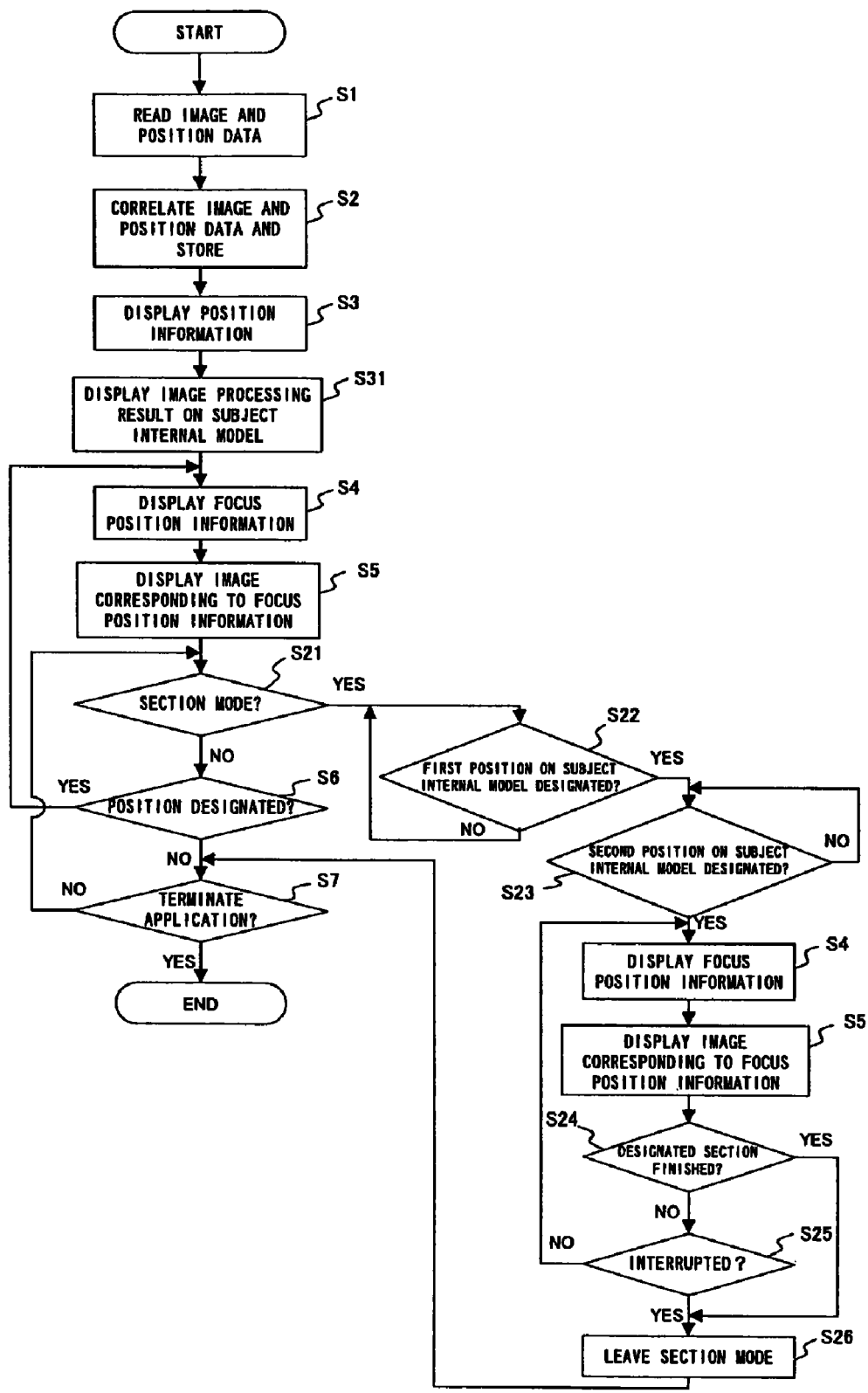
FIG. 5 is a flowchart explaining the operation of the image processing of the capsule endoscope image filing system relating to the second embodiment of the present invention.

FIG. 5 is a flowchart explaining the operation of the image processing in the second embodiment. This image processing is also processing performed by the CPU of the main device 19 based on the instruction input by a doctor or a nurse from the keyboard 22 or the mouse 23 of the workstation 7 shown in FIG. 1. In this case also, the operation explained in the first embodiment is performed in advance of this processing.

In FIG. 5, processing S1-S3, S4, and S5 are the same as the processing S1-S3, S4 and S5, respectively, of the first embodiment explained with the flowchart of FIG. 3. In the present embodiment, processing S31 is performed between the processing S3 and the processing S4.

Specifically, after the processing of displaying the focus position information (S3), a doctor or a nurse designates extraction of image data of an unusual image in advance of the processing. Based on the designation input, the second position mark 44 shown in FIG. 4A for example, is displayed on the trajectory path 37 in series (S31).

After the display of focus position information (S4) and the display of the image corresponding to the focus position information (S5), in the present embodiment, it is determined (S21) whether the section mode is designated or not.

In this process of determining whether the section mode is designated or not, for example, the setting of the section mode can be specified by a doctor or a nurse by pointing to a position other than the display of the trajectory path 37 on the display area 46 for displaying each model by the pointing arrow 43 and left-clicking the mouse 23. The above determination processing is to determine whether a left-click operation is performed or not at such a particular position. The section mode is a mode, in which all of the position information within an arbitrary section is regarded as focus position information.

When the instruction of the section mode setting is input (S21: YES), the CPU waits until a first position of the subject internal model 26 is designated (S22 and the determination is NO).

This is processing for determining whether or not the first position to designate the section on the display of the trajectory path 37 of the subject internal model 26 is designated by the pointing arrow 43 or not, as the first pointing arrow 43-1 designating the section shown in FIG. 4D, for example, and, if it is not designated, for repeating the determination until it is designated.

When the first position is designated (S22: YES), the CPU stores the information of the designated first position of the subject internal model 26 in a prescribed storage area of the built-in memory, and next, waits until the second position on the subject internal model 26 is designated (S23 and the determination is NO).

This is processing for determining whether or not the second section to designate the section on the display of the trajectory path 37 of the subject internal model 26 is designated by the pointing arrow 43 or not, as the second pointing arrow 43-2 designating the section shown in FIG. 2D, for example, and, if it is not designated, for repeating the determination until it is designated.

When the second position on the subject internal model 26 is designated (S23: YES), the CPU stores the information of the designated second position of the subject internal model 26 in another prescribed storage area of the built-in memory, performs processing S4 and processing S5 which is the same as the processing S4 and the processing S5, which follow the above processing S31, and determines whether the designated section is finished or not (S24).

This is processing to determine whether or not the above processing S4 and the processing S5 are performed on the position corresponding to information of the designated second position on the subject internal model 26 stored in the other prescribed storage area of the above built-in memory.

When the designated section is not finished (S24: NO), it is further determined (S25) whether or not interruption of the processing is requested.

In this processing, the interruption of the processing is requested by a doctor or a nurse pointing to a position other than the display of the trajectory path 37 on the model display area 46 by the pointing arrow 43 and right-clicking the mouse 23. The above determination processing is to determine whether or not the right-click operation of the mouse 23 is performed or not at such a position.

When the interruption of the processing is not instructed (S25: NO), the process returns to the processing S4, and the processing S4, the processing S5, the processing S24 and the processing S25 are repeated.

On the other hand, when an instruction for the interruption of the processing is detected (S25: YES), the processing to leave the section mode is performed (S26), and the process proceeds to the processing S7.

The above processing S26 is processing for deleting information of the designated first position and second position of the subject internal model 26 stored in the prescribed storage area and the other prescribed storage area of the above built-in memory, and for releasing the section mode setting.

When the designated section is finished for the determination processing of the above processing S24 (S24: YES), the process immediately proceeds to the above processing S26.

When the section mode setting is not specified in the section mode determination processing in the processing S21 (S21: NO), the CPU, next, performs the determination processing of the processing S6, which is the same as the processing of S6 shown in FIG. 3. In this case also, if the position is not designated (S6: YES), the process returns to the processing of S4, and the processing of S4 and the following steps is performed.

Meanwhile, when the position is not designated in the determination processing of the processing (S6: NO), the process proceeds to the processing S7, the determination processing for the termination of the application, is the same as the processing S7 shown in FIG. 3. When the termination of the application is not instructed, the process returns to the processing S21, performs the processing S21 and following steps, and when the termination of the application is instructed, the application is terminated.

By so doing, if a doctor or a nurse, looking at the display screen on the monitor device 21 of the workstation 7, designates any two positions on the trajectory path 37 of the subject internal model 26, by moving the pointing arrow 43 by the operation of the mouse 23, unless instructing the interruption of the processing, the position marks 39 are superimposed and displayed in series at the positions where images are captured from the beginning to the end of the section indicated by the designated two positions, and the images corresponding to the positions are displayed on the left side area of the same display screen.

At that time, in the image display area 41, an unusual image with a characteristic part 45 as the image 42 can be identified FIG. 6 is a flowchart explaining the operation of the image processing of the capsule endoscope image filing system relating to the third embodiment of the present invention. The image processing is processing performed by the CPU of the main device 19 based on the instruction input from the keyboard 22 or the mouse 23 of the workstation 7 shown in FIG. 1 by a doctor or a nurse. In this case also, the operation explained in the first embodiment is performed in advance of this processing.

In FIG. 6, the processing S1-S3 and the processing S4-S7 are the same as the processing S1-S7 explained in the flowchart in FIG. 3 of the first embodiment. In the present embodiment, the processing S31, which is the same as the processing shown in FIG. 5, is performed between the processing S3 and the processing S4 shown in the flowchart of FIG. 3.

In other words, after the processing of the display of the position information (S3), based on the designation of the extraction of the image data of the unusual image, which is the image comprising the characteristic part, by a doctor or a nurse in advance of the processing, the second position marks 44 shown in FIG. 4A, FIG. 4B, FIG. 4C and FIG. 4D, for example, are displayed on the trajectory path 37 in series (S31).

By so doing, the doctor or the nurse, operating the display screen, can designate the position mark 39 around the second position mark 44 and observe the image 42 of the position around the second position mark 44, while designating the position marks 39 in series and changing the image 42 displayed on the image display area 41.

Figure 7:
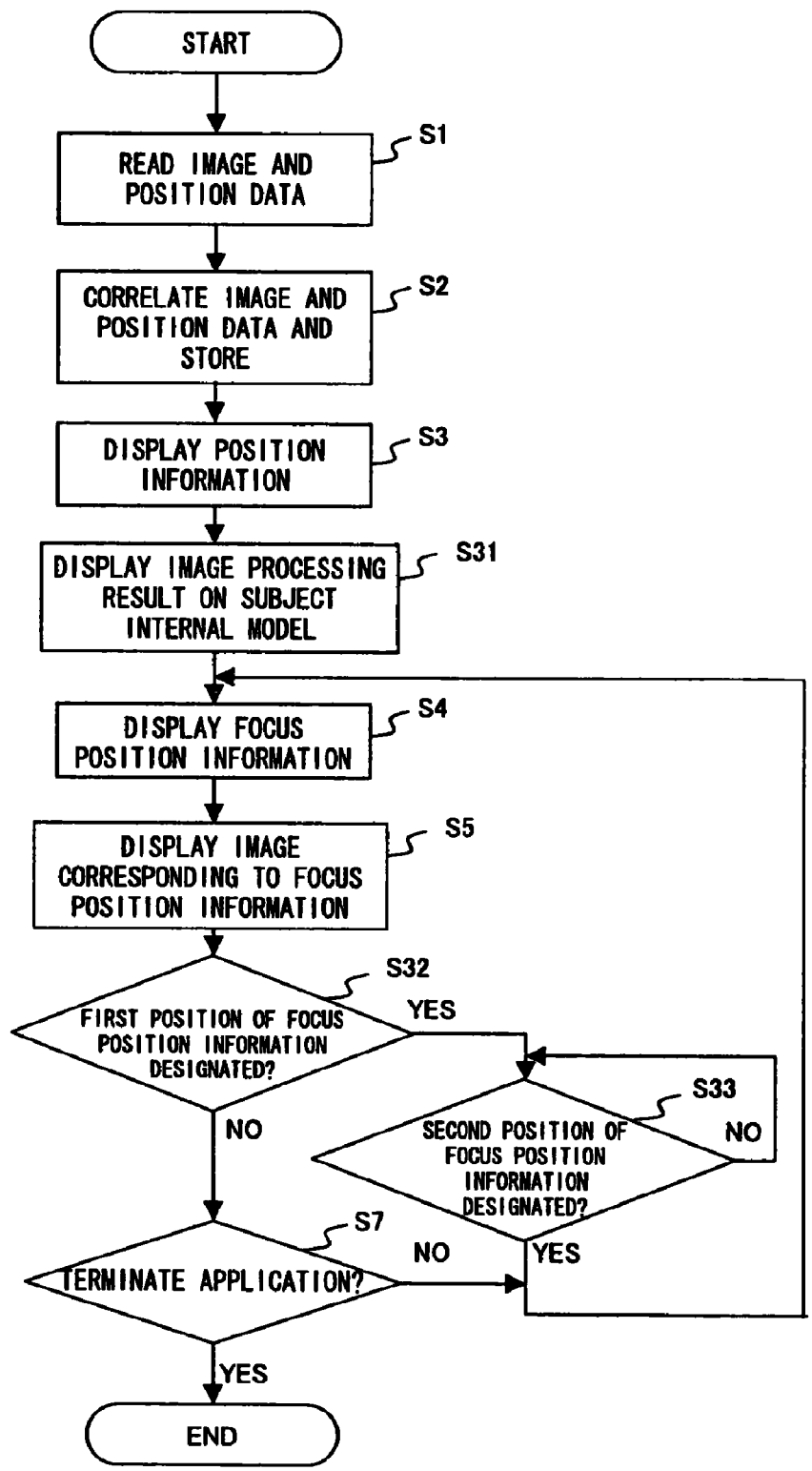
FIG. 7 is a flowchart explaining another example of the operation of the image processing of the third embodiment.

FIG. 7 is a flowchart explaining another example of the operation of the image processing in the third embodiment. In this processing, processing S32 and processing S33 are performed instead of the processing S6 shown in FIG. 6.

In other words, following the display of the first focus position information (S4) and the display of the image corresponding to the focus position information (S5), it is determined (S32) whether or not the first position of the focus position information is designated.

This processing is processing, in response to the input operation of the "section designation" menu or the "section designation" button by a doctor or a nurse operating the mouse 23, by the subsequent operation of the mouse 23, to determining whether or not any of the positions on the display of the trajectory path 37 of the subject internal model 26 is designated as the position to be focused on first in the above designated section, that is the first position.

When the first position, which is the position to be focused on first in a section, is not designated (S32: NO), the process returns to the processing S4 at the determination of the processing S7, and the processing S4, the processing S5, and the processing S32 are repeated.

When the first position, which is the position to be focused on first in the section, is designated (S32: YES), the CPU determines whether or not the second position of the focus position information is designated (S33).

This processing is to determine whether or not the second position designating the end of the section is designated on the display of the trajectory path 37 of the subject internal model 26 by the pointing arrow 43, as the second pointing arrow 43-2 designating the section shown in FIG. 2D, for example.

When the second position of the focus position information, which is the end position of the section, is not designated (S33: NO), the designation of the point is awaited, and when the second position of the focus position information is designated (S33: YES), the process returns to the processing S4, the process returns to the processing S4, the position mark 39 at the first position, designated as the first position, is displayed (focus position information display), additionally in the processing S5, the image 42 of the image data corresponding to the first position in the designated section on the display of the trajectory path 37 is displayed, whether the position is within the designated section or not is determined by the processing S32 and the processing S33, and if it is within the section, the process returns to the processing S4, and display of the position mark 39 and display of the image 42 are performed by the processing S4 and the processing S5.

When the process returns to the processing S4 for the first time, all position marks within the designated section are displayed, and in the processing S5, it is possible to display the images 42 corresponding to all the position marks 39 within a certain time interval in series or to display the images 42 at the position corresponding to the designated position mark 39 according to the designation by the pointing arrow 43.

By so doing, a doctor or a nurse can find the position of an intended unusual image with the characteristic part within the intended arbitrary sections on the display of the trajectory path 37 of the subject internal model 26, and can observe the images around the position including the unusual image in an arbitrary section.

Next, the processing operation of the image processing of the capsule endoscope image filing system of the fourth embodiment is explained.

Figure 8:
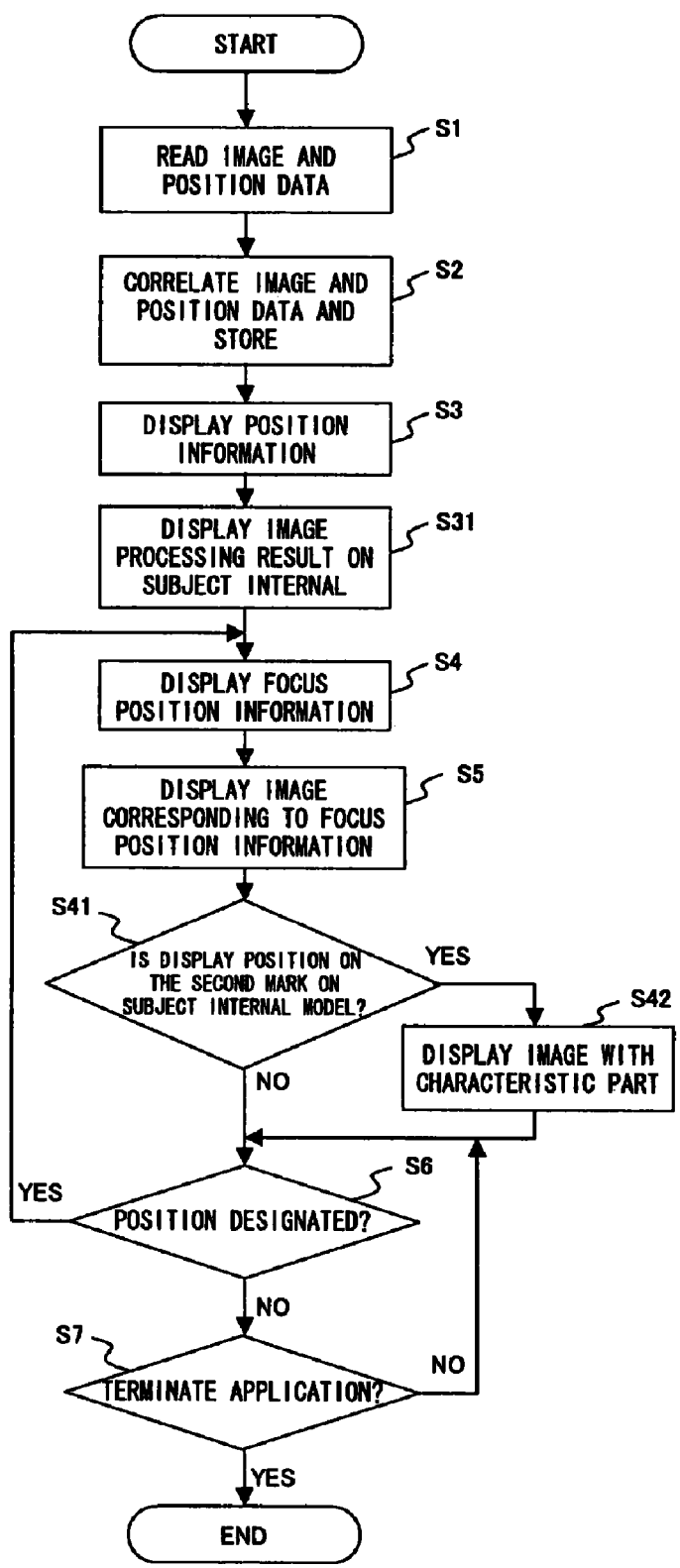
FIG. 8 is a flowchart explaining the operation of the image processing of the capsule endoscope image filing system relating to the fourth embodiment of the present invention.

FIG. 8 is a flowchart explaining the operation of the image processing of the fourth embodiment. This image processing is also performed by the CPU of the main device 19 based on the instruction input from the keyboard 22 or the mouse 23 of the workstation 7 shown in FIG. 1, by a doctor or a nurse. In this case also, the operation explained in the first embodiment is performed in advance of this processing.

In FIG. 8, the processing S1-S3, S31, S4, S5, S6, and S7 are the same as the processing of S1-S3, S31, S4-S7 as explained in the flowchart of FIG. 6 of the third embodiment. In the present embodiment, the processing S41 and the processing S42 are performed between the processing S5 and the processing S6 of the flowchart in FIG. 6.

In other words, in the stage of the first display of the focus position information (S4), the display of all second position marks 44 displayed by the processing S31 is superimposed on the display of the position mark 39 in the processing S4, and is displayed on the display of the trajectory path 37 of the subject internal model 26, and in the processing S5, the image 42 corresponding to the above position mark 39 is displayed on the image display area 41 on the right side.

The CPU, at that time, determines whether or not the display position of the position mark 39 is consistent with the display position of the second mark on the subject internal model 26 (S41).

This processing is to determine whether or not the display position, at which the above position mark 39 should be displayed, is superimposed on any of the second position marks 44 displayed on the model in the processing S31 (as explained in FIG. 4A and FIG. 4B, the number of displayed second position marks 44 is generally expected to be of a plural number rather than only one as shown in the drawings, and therefore in the actual display, all of a plurality of the second position marks 44 are displayed on the display of the trajectory path 37).

When the display position is not superimposed on that of the second position mark 44 (S41: NO), the process proceeds to the processing S6; however if it is superimposed on any of the display position of the second position mark 44 (S41: YES), the process proceeds to the processing S6 after displaying the image 42 with the characteristic part (S42).

In the above processing S42, the image 42 at the position, indicated by the second position mark 44 superimposed on the display position of the position mark 39, as shown in FIG. 4B for example, is displayed on the image display area 41. As further shown in FIG. 4C, the characteristic part 45, which caused the image 42 to be extracted from the database 9, is displayed, being superimposed on the displayed image 42.

The following processing S6 and processing S7 are the same as in FIG. 3, FIG. 5 and FIG. 6.

By such processing, a doctor or a nurse can designate a second position mark 44 at an arbitrary position among the second position markers 44 indicating the image capture position of the unusual image which are all displayed on the trajectory path 37, and can immediately locate and observe the entire unusual image (the image 42 in FIG. 4B) and the position of the unusual condition (the characteristic part 45 in FIG. 4C).

Next, the processing operation of the image processing of the capsule endoscope image filing system in the fifth embodiment is explained.

FIG. 9 is a flowchart explaining the operation of the image processing in the fifth embodiment. This image processing is also performed by the CPU of the main device 19 based on the instruction input from the keyboard 22 or the mouse 23 of the workstation 7 shown in FIG. 1 by a doctor or a nurse. In this case also, the operation explained in the first embodiment is performed in advance of this processing.

In FIG. 9, the processing S1-S3, S31, S4, S5, S41, S42, S6, and S7 are the same as the processing S1-3, S31, S4, S5, S41, S42, S6 and S7, respectively, as explained in the fourth embodiment with the flowchart in FIG. 8. In the present embodiment, unlike the case of FIG. 8, the processing S21-S26 (including the processing S4, S5, S41 and S42 in the middle) are performed immediately before the processing S6.

In the processing S21-S26, explaining in the order of the processing, the processing S21-S23, S4 and S5 are the same the processing S21-S23, S4 and S5 shown in FIG. 5, the following processing S41 and S42 are the same as the processing S41 and S42 shown in FIG. 8 and further, the following processing S24, S25 and S26 are the same as the processing S24, S25 and S26 shown in FIG. 5.

By the above processing, a doctor or a nurse, by designating the condition of the lesion obtained according to the symptom (for example, conditions of the bleeding part or conditions of a polyp), and by designating an arbitrary section of interest on the display of the trajectory path 37 of the subject internal model 26, can display the image 42 which constitutes an unusual image, which is an image corresponding to the position of the second position mark 44 within the section, and can immediately determine how extensive the symptom is and how severe the symptom is etc. by observing the characteristic part 45, which is the part of the image with an unusual condition.

In such a manner, according to the image processor and the image processing method of the capsule endoscope image filing system of the present invention, both an image and the image capture position can be observed on the same display screen in association with the image and the image capture position, and furthermore, an image at any intended position can be immediately observed by a simple operation of a mouse.

In addition, for the symptoms of concern, by designating the known conditions of color, which are unique to the symptom, of the intra-luminal observation as prepared color information etc., images with the same or the similar conditions of color are detected, those images and their image capture positions can be observed, and consequently an accurate and immediate decision can be made.

In the above example, the trajectory path 37 of the capsule endoscope 3 as position information is displayed in three dimensions in relation to the actual shape of the luminal tract (although the display is two dimensional, it appears to be three dimensional on the actual display screen in accordance with the shape of the luminal tract); however, it is not limited to this display, but the position information can be represented by a two dimensional plane, or by one dimension, that is a line. When representing the position information in one dimension, sections corresponding to the esophagus 31, the stomach 32, the duodenum 33, the small intestine 34, the large intestine 35, the rectum 36 and so forth shown in FIG. 2A should be established on the line, and then, the positions can be displayed.

<Sixth Embodiment>

FIG. 10A, FIG. 10B and FIG. 10C are diagrams showing the luminal organ model 26 and the image 42 of the subject individual 4, displayed on one display screen 38 of the monitor device 21 of the workstation 7 in the capsule endoscope image filing system relating to the sixth embodiment of the present invention. FIG. 10A is, as is FIG. 2A, a diagram showing the luminal organ model of the subject individual 4 displayed on the display screen of the monitor device 21, and FIG. 10B and FIG. 10C are diagrams showing examples of images displayed on one display screen of the monitor device 21 as well as the luminal organ model. In FIG. 10B and FIG. 10C, the luminal organ model shown in FIG. 10A is simplified for convenience of explanation.

The reference numerals in FIG. 10A, FIG. 10B and FIG. 10C are the same as those of FIG. 2A, FIG. 2B, FIG. 2C and FIG. 2D.

As shown in FIG. 10A, the luminal organ model 26 of the subject individual 4 is displayed as a two-dimensional diagram with a body outline 27 of the subject individual 4 and a luminal organ outline 28. The luminal organ outline 28 displays the outline of the esophagus 31, the stomach 32, the duodenum 33, the small intestine 34, the large intestine 35, the rectum 36 and so forth. The trajectory path 37 of the capsule endoscope 3 is displayed in the luminal organ outline 28.

As shown in FIG. 10B, on the display screen 38 of the monitor device 21, the above luminal organ model 26 is displayed on the left side of the same screen, and on its trajectory path 37 of the capsule endoscope 3, the position mark 39 as focus position information among position information indicating image capture positions is superimposed and displayed. In the image display area 41 on the right side of where the luminal organ model 26 is displayed, the image 42 captured on the trajectory path 37 corresponding to the position mark 39 is displayed.

FIG. 10C shows an example displaying the pointing arrow 43 by the operation of the mouse 23 pointing at the displayed position mark 39.

Next, the image processing in the above capsule endoscope image filing system in the sixth embodiment is explained.

Figure 11:
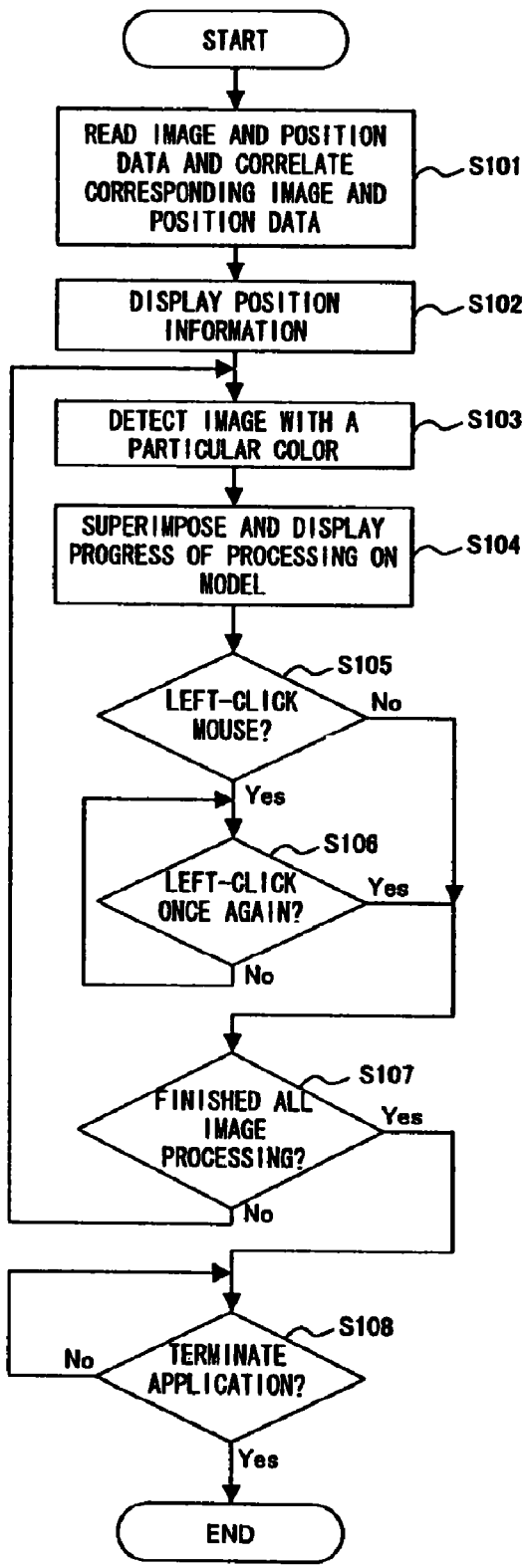
FIG. 11 is a flowchart explaining the operation of the image processing of the capsule endoscope image filing system relating to the sixth embodiment of the present invention.

FIG. 11 is a flowchart explaining the operation of the image processing in the sixth embodiment. This image processing is processing performed by a control device incorporated in the main device 19 (hereinafter referred to as CPU) based on the instruction input from the keyboard 22 or the mouse 23 of the workstation 7 shown in FIG. 1 by a doctor or a nurse.

The following operation is performed in advance of the processing. That is, the capsule endoscope 3 is removed from the package 2 by the subject individual 4, the power switch of the capsule endoscope 3 is turned on, and the conditions of the luminal organs of the subject individual 4 are successively captured by the imaging unit of the capsule endoscope 3, during the time period from the capsule endoscope 3 being swallowed by the subject individual 4 until it is passed out of the body by the automatic movement.

The captured image data is transmitted from the wireless unit of the capsule endoscope 3 as a radio signal (an image signal), and the transmission is received by the antenna 11 (11a, 11b, 11c and 11d) of the jacket 5. The received signal is transferred to the receiver 6.

The receiver 6 performs reception from each antenna 11 in rotation by switching and generates one frame of signal in sequence, pairing the radio intensity of the image signal and the signal content (image data) of the image signal. In other words, five frames of signals are generated from one piece of image data. The generated five frames of signals are stored in the CF memory 17 in series. The processing on the receiver 6 side is repeated for every image capture during the successive capture of the capsule endoscope 3.

In FIG. 11, the CPU, first, reads the image data and the position data, and stores the read image data and the position data in such a way that they are correlated with each other (S101).

In this processing, the CPU reads the received data stored in the CF memory 17, directly from the receiver 6 by wire or from the CF memory attached to the CF memory reader/writer 25 removed from the receiver 6 five frames at a time.

The image data is read out from the received data of the antenna 11, which has the strongest received radio wave (i.e. the antenna which is the closest to the capsule endoscope 3), for example, and additionally among the five frames of received data, the transmission position of the image signal corresponding to the above image data is calculated from the five radio intensities corresponding to each antenna, and the calculated transmission position (the image capture position) data is acquired as focus position information.

A record with the acquired interrelated image data and focus position information as a pair is generated, and the record is registered in the database 9.

Next, the CPU displays the schematized position information (S102).

This processing is processing for displaying the luminal organ model 26 as shown in FIG. 10A, FIG. 10B and FIG. 10C on the display screen of the monitor device 21 of the workstation 7. The above schematized position information refers to the trajectory path 37 of the capsule endoscope 3 in the luminal organ model 26.

Following the above processing, the CPU detects an image with a particular color (S103).

This processing is processing, when image data with a particular color designated by a doctor or a nurse in advance is detected in the process of a sequential search of the above database 9, for storing the focus position information of the detected image data. By so doing, various collective processing of the above particular image can be performed, if required, after the termination of the present application.

The above particular color might be the color of bleeding in the luminal organ, for example. Bleeding is a phenomenon, which occurs in diseased areas, and in general, the color of the blood during or immediately after bleeding is a significantly vivid red. For that reason, a doctor or a nurse designating the color information corresponding to the color of blood in advance, the CPU can readily detect an image with a bleeding area (a diseased area) by comparing the designated color information.

Next, the CPU superimposes and displays the progress of the above image processing (the particular image detection processing) of the model (the luminal organ model 26) (S104).

This processing is for displaying the position mark 39 by superimposing it on the position information on the display screen of the above monitor device 21, that is on the display of the trajectory path 37 (see FIG. 10B and FIG. 10C). The position mark 39 indicates the position in the luminal organ model 26 where the images being processed are captured in order to detect the above image with the diseased area.

Next, the CPU determines whether the left button of the mouse 23 is clicked or not (S105). In this processing, if the left button of the mouse 23 is clicked (S105: YES), it signifies instruction for suspension of processing in this embodiment, and therefore the CPU suspends the above processing and waits until the left button of the mouse 23 is clicked once again (S106: NO).

When the left button of the mouse 23 is clicked once again (S106: YES), whether all image processing is finished or not is determined (S107).

The CPU, when the left button of the mouse 23 is not clicked in the above determination processing of S105 (S105: NO), immediately moves to the above processing S107.

The above processing S107 is processing for determining whether the above search processing on all images of luminal organs of the subject individual 4, successively captured by the imaging unit of the capsule endoscope 3 and stored in the database 9, is finished or not during the time period that the capsule endoscope 3 is swallowed by the subject individual 4 until it is passed out of the body after automatic movement.

If all the images are not yet finished (S107: NO), the process returns to the processing S103 and the processing S103-S107 is repeated. By so doing, as the above processing progresses, in the processing S104, the position mark 39 indicating the current processing position is superimposed and displayed on the display of the trajectory path 37, while moving sequentially on the display of the trajectory path 37 in the luminal organs.

When the above search processing is finished on all images (S107: Yes), the CPU waits for the instruction of application termination (S108, No discrimination), confirms the instruction of the application termination (S108: Yes), and terminates the application.

The above processing to determine the termination of the application, for example, is performed by preparing the terminate button, not shown in the drawings, for instruction and execution of the termination of the application and by having a doctor or a nurse etc. instructing with a left click of the terminate button by the mouse 23.

<Seventh-Ninth Embodiment>

FIG. 12A and FIG. 12B are diagrams of examples of the luminal organ model 26 of the subject individual and the image 42, both of which are displayed on one display screen 38 of the monitor device 21 of the workstation 7 in the capsule endoscope image filing system relating to the seventh-the ninth embodiment of the present invention.

If there is an unusual image etc. with a specific characteristic (for example, bleeding, of a particular color) indicating the symptom designated by a doctor or a nurse in advance, the database 9 is searched based on the instruction input to display the unusual image, and, when image data containing the unusual image with the above specific characteristics is detected, the image display area 41 on the right side of the display screen 38 of the monitor device 21 shown in FIG. 12A displays the unusual image 42' of the detected image data.

The luminal organ model 26 on the left side of the display screen 38 shown in FIG. 12A, also, provides an example that an image processing result 44, which indicates a position where the detected unusual images are captured, is superimposed on the trajectory path 37 with the position mark 39 indicating a progress of the processing if there is an unusual image etc. with a specific characteristic (for example, bleeding) indicating the symptom designated by a doctor or a nurse in advance.

The display of the image processing result 44 is only displayed on one position in FIG. 12A; however in the actual display, the image processing result 44 of all unusual image data detected by the above search is displayed at the positions on the trajectory path 37 where the unusual images are captured.

Next, FIG. 12B shows an example where the image processing result 44 at a position is designated among the image processing results 44 indicating the image capture positions of all unusual images displayed on the above trajectory path 37 (although only one of the image processing result 44 in FIG. 12B is displayed, all image processing results 44 are displayed in the actual display) by the pointing arrow 43, the unusual image 42', based on the image data corresponding to the position (the position on the trajectory path 37, same applies to the following description) where the designated image processing result 44 is displayed, is displayed on the image display area 41 on the right side.

FIG. 12B is an example where the characteristic detection target position 45 (for example, a bleeding site), which is the cause of the detection of the unusual image 42' from the database 9, is displayed, superimposing the unusual image 42' displayed on the image display area 41 on the right side corresponding to the image processing result 44 in displaying the unusual image.

In the next description, the processing operation of the image processing in the capsule endoscope image filing system in the seventh embodiment is explained.

Figure 13:
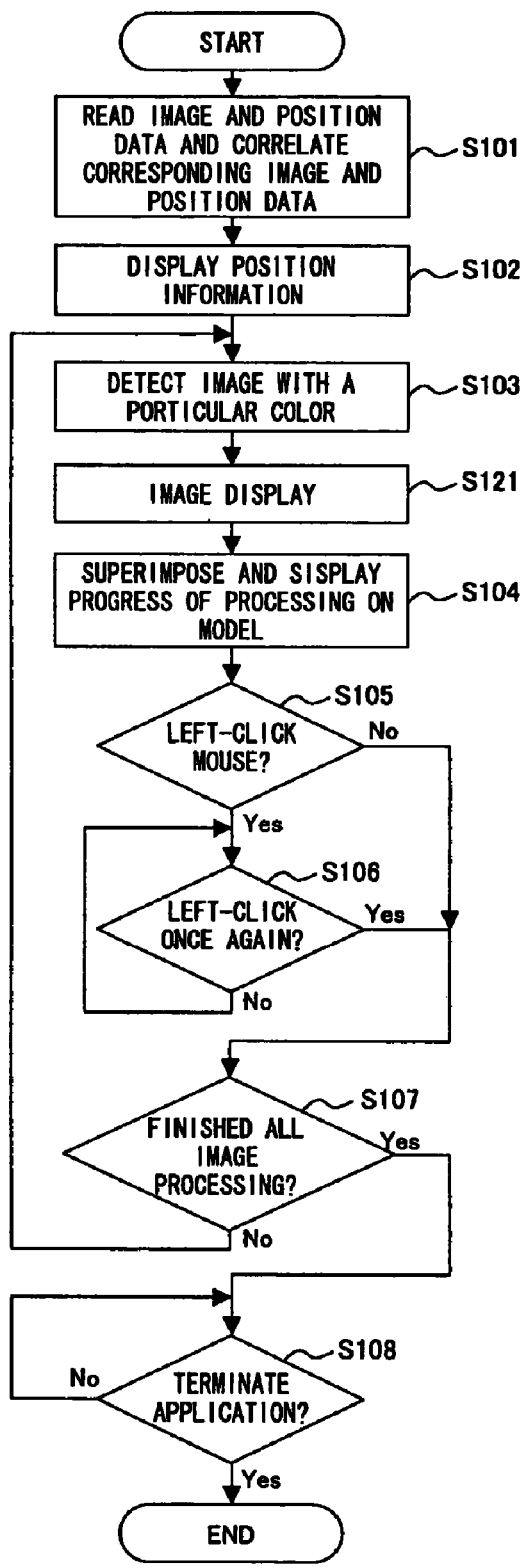
FIG. 13 is a flowchart explaining the operation of the image processing of the capsule endoscope image filing system relating to the seventh embodiment.

FIG. 13 is a flowchart explaining the operation of the image processing in the seventh embodiment. The image processing is processing performed by the CPU of the main device 19 based on the instruction input from the keyboard 22 or the mouse 23 of the workstation 7 shown in FIG. 1 of a doctor or a nurse. In this case also, the operation explained in the sixth embodiment is performed in advance of the processing.

In FIG. 13, the processing S101-S103 and S104-S108 are the same as the processing S101-S108, respectively, as explained in the first embodiment with the flowchart in FIG. 11. In the present embodiment, the processing S121 is performed between the processing S103 and the processing S104.

In other words, the CPU, after detecting an unusual image with a particular color in the processing S103, displays the detected unusual image as in the unusual image 42' shown in FIG. 12A, for example. The display time is longer than two seconds for one unusual image 42', for example. In parallel with the display, proceeding with the search for the next unusual image, the current search position is displayed sequentially, superimposed on the trajectory path 37, like the position mark 39 shown in FIG. 12A, for example.

The position mark 39 can be displayed only at the current search position (in other words, the display of the position mark 39 moves along with the movement of the current search position), or alternatively, the position mark 39 once displayed, can remain displayed and the number of the display of the position mark 39 can be increased according to the movement of the current search position.

In either case, for a doctor or a nurse, the conditions of abnormality occurrence in the luminal organ model 26 is visible along with the trajectory path 37, and also the progress of the image search processing is visible at a glance by the position mark display of the current search position, and for those reasons, a decision for the next treatment can be made immediately.

Next, the processing operation of the image processing in the capsule endoscope image filing system in the eighth embodiment is explained.

Figure 14:
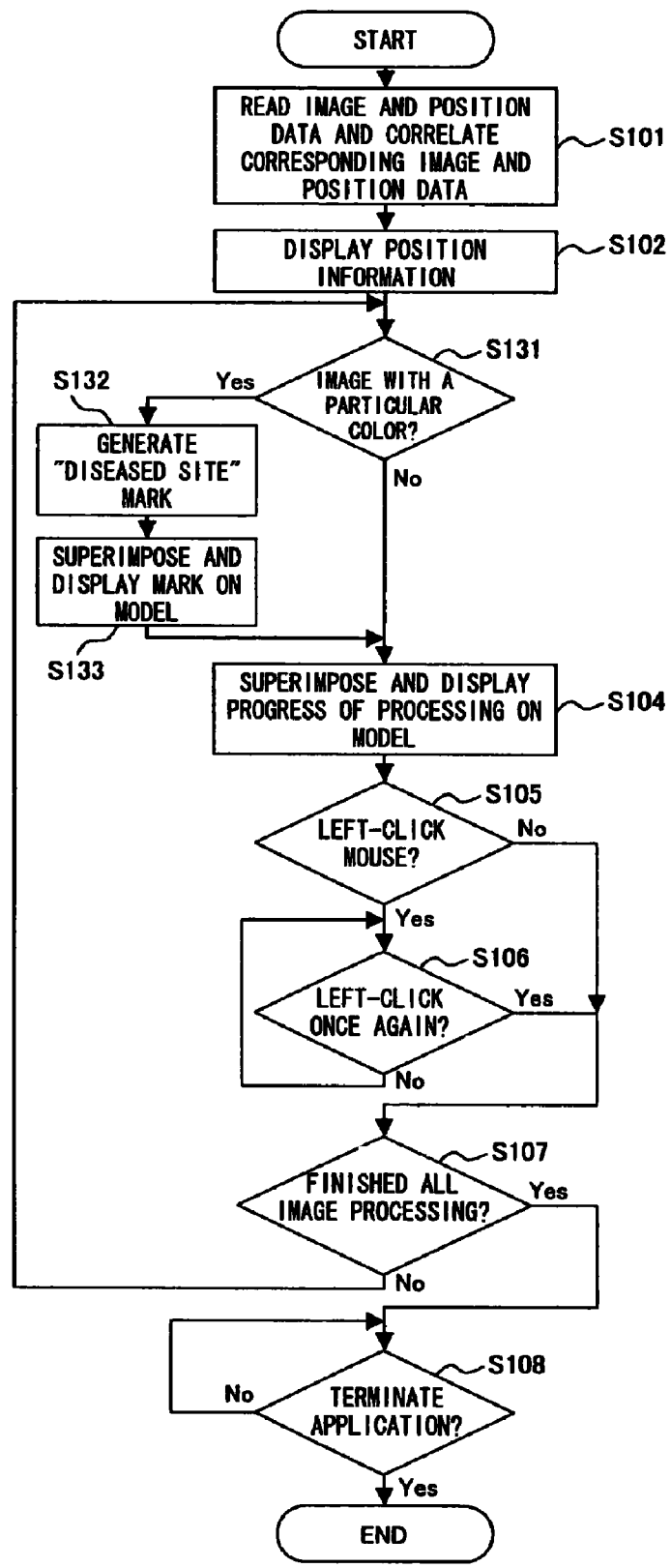
FIG. 14 is a flowchart explaining the operation of the image processing of the capsule endoscope image filing system relating to the eighth embodiment of the present invention.

FIG. 14 is a flowchart explaining the operation of the image processing in the eighth embodiment. The image processing is also processing performed by the CPU of the main device 19 based on the instruction input from the keyboard 22 or the mouse 23 of the workstation 7 shown in FIG. 1 by a doctor or a nurse. In this case also, the operation explained in the sixth embodiment is performed in advance of the processing.

In FIG. 14, the processing S101, S102, S104-S108 are the same as the processing S101, S102, S104-S108, respectively, explained in the sixth embodiment with the flowchart in FIG. 11. In the present embodiment, the processing S131-S133 is performed instead of the processing S103 in the flowchart in FIG. 11.

In other words, following the display of the schematized position information in the processing S102 (the display of the luminal organ model 26 of the subject individual 4 displayed on the left side area of the display screen 38 of the monitor device 21), the CPU determines whether, in the image data processing of the current search position, unusual image data with a particular color (for example the color of bleeding) designated by a doctor or a nurse in advance is detected or not (S131).

If such unusual image data with the particular color is not detected (S131: No), the process proceeds to the processing S104; however if the unusual image data with the particular color is detected (S131: Yes), first, a mark indicating "diseased site" is generated (S132).

The mark indicating "diseased site" is the same as in the image processing result 44 shown in FIG. 12A and FIG. 12B. In other words, the image processing result 44 shown in FIG. 12A and FIG. 12B shows the diseased site marks.

Following the above process, the CPU displays the above generated diseased site marks (image processing result 44), superimposed on the model (S133).

By so doing, as shown in the image processing result 44 in FIG. 12A and FIG. 12B for example, the mark indicating the diseased site is displayed at the diseased position, superimposed on the trajectory path 37 of the capsule endoscope 3 of the luminal organ model 26, and, for a doctor or a nurse, the spread range of the diseased sites is visible at a glance.

Next, the processing operation of the image processing of the capsule endoscope image filing system of the ninth embodiment is explained.

Figure 15:
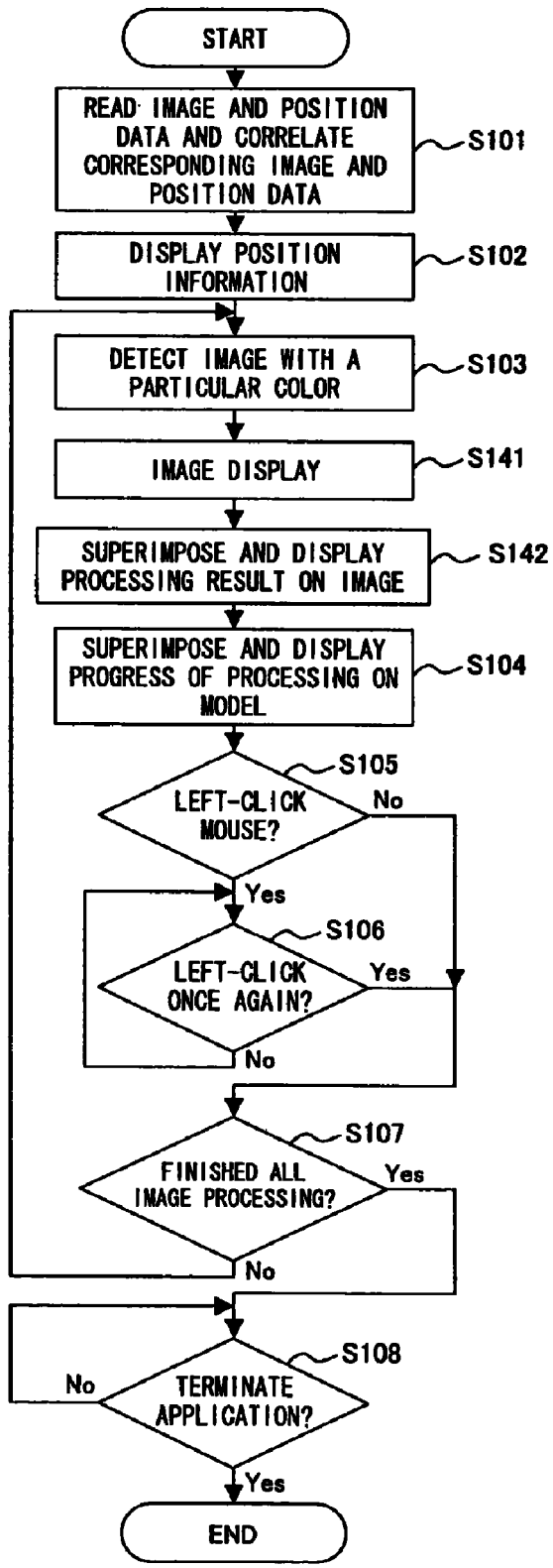
FIG. 15 is a flowchart explaining the operation of the image processing of the capsule endoscope image filing system relating to the ninth embodiment of the present invention.

FIG. 15 is a flowchart explaining the operation of the image processing of the ninth embodiment. The image processing is also processing performed by the CPU of the main device 19 based on the instruction input from the keyboard 22 or the mouse 23 of the workstation 7 shown in FIG. 1 by a doctor or a nurse. In this case also, the operation explained in the sixth embodiment is performed in advance of the processing.

In FIG. 15, the processing S101-S103, S104-S108 is the same as the processing S101-S103, S104-S108, respectively, explained in the sixth embodiment with the flowchart in FIG. 11. In the present embodiment, the processing S141 and the processing S142 are performed between the processing S103 and the processing S104 in the flowchart in FIG. 11.

In other words, after detecting an unusual image data with a particular color in the processing S103, the CPU displays images (S141).

In the image display processing, the unusual image of the above-detected unusual image data is displayed on the image display area 41 of the display screen 38 of the monitor device 21, in the same way as the unusual image 42' shown in FIG. 12B, for example.

In addition, the CPU superimposes and displays the processing result on the image (S142).

This processing is for displaying the diseased position, which was the cause of detection of the unusual image 42' from the database 9 as the above image processing result, superimposing the position on the display of the unusual image, like the characteristic detection target position 45 shown in FIG. 12B, for example.

By so doing, a doctor or a nurse can immediately perceive the diseased site by the display of the characteristic detection target position 45 and can immediately start detailed examination of the diseased site without being troubled with looking for the diseased site on his/her own from the displayed unusual image.

In this processing, a doctor or a nurse can skip the processing at any time by the operation of the mouse, moving the pointing arrow 43 along the display of the trajectory path 37 of the luminal organ model 26, and left-clicking at the desired position, and can resume the processing from the left-clicked position. Further, the position mark 39, at that time, moves to the designated position.

In the above example, the trajectory path 37 of the capsule endoscope 3 is displayed according to the shape of the actual luminal organs; however, it is not limited to this shape, but the display can be, for example, one-dimensional, that is a line, as position information, and the position can be displayed by establishing the sections corresponding to the esophagus 31, the stomach 32, the duodenum 33, the small intestine 34, the large intestine 35, the rectum 36 and so forth shown in FIG. 10A on the line.

As explained above, according to the above-described embodiments of the present invention, it is possible to easily comprehend a large number of image information, and to easily locate the image information of intended positions, diseased sites and others, to be focused on from a large number of image information.

It is convenient that the part of the body to which the image processing has proceeded can be intuitively comprehended because, unlike the common display by a progress bar, the position information of the luminal organs is schematized in one or higher dimensions and is displayed, and the progress of the image processing is superimposed and displayed on the display of the schematized position information.

In addition, it is convenient that the part of the body at which a particular condition occurs can be easily perceived because a particular display showing the processing result of a particular image is superimposed and displayed on the display of the position information, and the particular image is displayed on the image display area of one screen.

Furthermore, image processing control is performed by operating a mouse directly on the display of the position information, and thus it is possible to perform operations intuitively in relation to the positions in the luminal organs, providing simple operation and convenience.

What is claimed is:

1. A display processor of image information for causing a display unit to display a plurality of image information acquired by capturing images over time at a plurality of positions in a subject body by an imaging device introduced into the subject body, the display processor comprising:
    an image information acquisition unit for acquiring a plurality of the image information;
    a position information acquisition unit for acquiring a plurality of position information, correlated with each of a plurality of the image information and relating to each position in the subject body where the imaging device captured images over time;
    a storage unit for correlating and storing the image information and the position information;
    a position information display unit for causing the display unit to display, based on a plurality of the position information stored by the storage unit, the position where the imaging device captured images over time, as a diagram in at least two dimensions which is schematization of a luminal organ and which includes a body outline and a luminal organ outline;
    a focus position information instruction unit for indicating at least one among a plurality of the position information as focus position information;
    an image display unit for causing the display device to display image information correlated with the position information indicated as the focus position information among a plurality of the position information displayed as diagrams;
    an acquisition unit for acquiring image information including a designated characteristic part based on information that is unique to the designated characteristic part; and
    a characteristic image detection unit for extracting the image information including the designated characteristic part acquired by the acquisition unit among a plurality of the image information,
    wherein:
        the focus position information instruction unit designates position information, relating to the image information including the designated characteristic part extracted by the characteristic image detection unit, as the focus position information, and
        the focus position information instruction unit causes a position indicated by the focus position information to be displayed on the diagram displayed by the display unit.

2. The display processor of image information according to claim 1, further comprising a position mark display unit for displaying a prescribed mark at a position corresponding to the focus position information in the diagram among a plurality of position information displayed as a diagram by the position information display unit.

3. The display processor of image information according to claim 1, wherein the focus position information designation unit further comprises a designated position input unit for designating arbitrary position information on the diagram as the focus position information among a plurality of position information displayed as the diagram by the position information display unit.

4. The display processor of image information according to claim 1, wherein the image display unit causes the image information including the designated characteristic part acquired by the acquisition unit to be displayed in such a way that a position of the designated characteristic part is superimposed on this image information.

5. A display processing method of image information for displaying a plurality of image information acquired by capturing images at a plurality of positions in a body over time on a display screen of a monitor device, the display processing method comprising:
    an image information acquisition process for acquiring a plurality of the image information;
    a position information acquisition process for acquiring a plurality of position information, correlated with each of a plurality of the image information and relating to each position in the subject body where the imaging device captured images over time;
    a storage process for correlating and storing the image information and the position information;
    a position information display process for causing the display screen of the monitor device to display, based on a plurality of the position information stored by the storage process, the position where the imaging device captured images over time, as a diagram in at least two dimensions which is schematization of a luminal organ and which includes a body outline and a luminal organ outline;
    a focus position information instruction process for indicating at least one among a plurality of the position information as focus position information;
    an image display process for causing the display screen of the monitor device to display image information correlated with the position information indicated as the focus position information among a plurality of the position information displayed as diagrams;
    an acquisition processing for acquiring image information including a designated characteristic part based on information that is unique to the designated characteristic part; and
    a characteristic image detection process for extracting the image information including the designated characteristic part acquired by the acquisition process among a plurality of the image information,
    wherein:
        the focus position information instruction process designates position information, relating to the image information including the designated characteristic part extracted by the characteristic image detection process, as the focus position information, and the focus position information instruction process causes a position indicated by the focus position information to be displayed on the diagram displayed by the image display process.

6. The display processing method of image information according to claim 5, further comprising a position mark display process for displaying a prescribed mark at a position corresponding to the focus position information in the diagram among a plurality of position information displayed as a diagram by the position information display unit.

7. The display processing method of image information according to claim 5, wherein the focus position information designation process further comprises a designated position input process for designating arbitrary position information on the diagram among a plurality of position information displayed as the diagram by the position information display process.

8. The display processing method of image information according to claim 5,
wherein the image display process causes the image information including the designated characteristic part acquired by the acquisition process to be displayed in such a way that a position of the designated characteristic part is superimposed on this image information.

9. A non-transitory recording medium for recording a display processing program for displaying a plurality of image information, acquired by capturing images at a plurality of positions over time in a subject body on a display screen of a monitor device by a computer, wherein the display processing program, by being executed by the computer, causes the computer to perform:
image information acquisition processing for acquiring a plurality of the image information;
position information acquisition processing for acquiring a plurality of position information, correlated with each of a plurality of the image information and relating to each position of which an image was captured over time in the subject body;
storage processing for correlating and storing the image information and the position information;
position information display processing for causing to display, based on a plurality of the position information stored by the storage processing, the position at which images were captured over time in the subject body, as a diagram in at least two dimensions which is schematization of a luminal organ and which includes a body outline and a luminal organ outline;
focus position information instruction processing for indicating at least one among a plurality of the position information as focus position information;
image display processing for causing display of image information correlated with the position information instructed as the focus position information among a plurality of the position information displayed as diagrams;
acquisition processing for acquiring image information including a designated characteristic part based on information that is unique to the designated characteristic part; and
characteristic image detection processing for extracting the image information including the designated characteristic part acquired by the acquisition processing among a plurality of the image information,
wherein:
the focus position information instruction processing causes the computer to perform processing for designating position information, relating to the image information including the designated characteristic part extracted by the characteristic image detection processing, as the focus position information, and
the focus position information instruction processing causes a position indicated by the focus position information to be displayed on the diagram displayed by the image display processing.

10. The recording medium according to claim 9 wherein the display program, by being executed by the computer, further causes the computer to perform position mark processing for displaying a prescribed mark at positions corresponding to the focus position information in the diagram among a plurality of position information displayed by the position information display processing as the diagram.

11. The recording medium according to claim 9, wherein the focus position information designation processing causes the computer to further perform designate position input processing for designating arbitrary position information in the diagram as the focus position information among a plurality of the position information displayed as the diagram by the position information display processing.

12. The recording medium according to claim 9, wherein the image display processing causes the image information including the designated characteristic part acquired by the acquisition processing to be displayed in such a way that a position of the designated characteristic part is superimposed on this image information.

13. An image filing device for a capsule endoscope for processing successive image data captured in succession by a capsule endoscope moving in a subject body at a prescribed time interval, the image filing device comprising:
a focus position information acquisition unit for acquiring an arbitrary position from one or more of position information relating to the position in the subject body where the successive image data is acquired as focus position information;
an image information acquisition unit for acquiring image information corresponding to the position designated as the focus position information from the successive image data;
a storage unit for correlating and storing the image information and the position information;
a position display unit for displaying one or more of position information in the subject body as a diagram in at least two dimensions which is schematization of a luminal organ and which includes a body outline and a luminal organ outline, based on the position information stored by the storage unit;
an image information processing unit for applying a prescribed processing to the image information acquired by the image information acquisition unit;
a progress information display unit for superimposing and displaying the position of the focus position information acquired by the focus position information acquisition unit, on the diagram displayed by the position display unit, and for indicating the progress of processing by the image information processing unit by changing display of the focus position information on the diagram;
a designated characteristic part acquisition unit for acquiring image information including a designated characteristic part based on information that is unique to the designated characteristic part; and
a characteristic image detection unit for extracting the image information including the designated characteristic part acquired by the designated characteristic part acquisition unit among a plurality of the image information, wherein:

the focus position information acquisition unit acquires a position, relating to the image information including the designated characteristic part extracted by the characteristic image detection unit, as the focus position information, and the focus position information acquisition unit causes a position indicated by the focus position information to be displayed on the diagram displayed by the position display unit.

14. The image filing device for a capsule endoscope according to claim 13, wherein the position display unit displays a trajectory path of the capsule endoscope in one or more luminal organs in the subject body while displaying the average locations of one or more internal organs in the subject body as a background of the trajectory path.

15. The image filing device for a capsule endoscope according to claim 13, wherein the progress information display unit superimposes and displays the display indicating the progress and the processing result of the image information processing unit on the display of the position display unit.

16. The image filing device for a capsule endoscope according to claim 13, further comprising an image information display unit for displaying progress of processing of the image information processing unit and image information corresponding to the processing of the image information processing unit.

17. The image filing device for a capsule endoscope according to claim 16, wherein the image information display unit displays the processing result of the image information processing unit in such a way that the display is superimposed on the display of the image information.

18. The image filing device for a capsule endoscope according to claim 16, wherein the image information display unit updates and displays the image information at a prescribed time interval.

19. The image filing device for a capsule endoscope according to claim 13, further comprising an instruction input unit for receiving an instruction from a device-operator, and wherein the image information processing unit performs a control of the image information processing based on the input result of the instruction input unit.

20. The image filing device for a capsule endoscope according to claim 19, wherein the control of the image information processing in the image information processing unit based on the input result from the instruction input unit is the end of the processing.

21. The image filing device for a capsule endoscope according to claim 19, wherein the control of the image information processing in the image information processing unit based on the input result from the instruction input unit is the suspension of the processing.

22. The image filing device for a capsule endoscope according to claim 19, wherein the control of the image information processing in the image information processing unit based on the input result from the instruction input unit is the resumption of the processing.

23. The image filing device for a capsule endoscope according to claim 19, wherein the control of the image information processing in the image information processing unit based on the input result from the instruction input unit is the change in the image information to be processed.

24. An image filing method for a capsule endoscope for processing successive image data captured in succession by a capsule endoscope moving in a subject body at a prescribed time interval, the image filing method comprising:

a focus position information acquisition process for acquiring an arbitrary position from one or more of position information relating to the position in the subject body where the successive image data is acquired as focus position information;

an image information acquisition process for acquiring image information corresponding to the position designated as the focus position information from the successive image data;

a storage process for correlating and storing the image information and the position information;

a position display process for displaying one or more of position information in the subject body as a diagram in at least two dimensions which is schematization of a luminal organ and which includes a body outline and a luminal organ outline, based on the position information stored by the storage process;

an image information processing process for applying a prescribed processing to the image information acquired by the image information acquisition process; and a progress information display process for superimposing and displaying the position of the focus position information acquired by the focus position information acquisition process on the diagram displayed by the position display process, and for indicating the progress of processing by the image information processing process by changing display of the focus position information on the diagram;

a designated characteristic part acquisition process for acquiring image information including a designated characteristic part based on information that is unique to the designated characteristic part; and a characteristic image detection process for extracting the image information including the designated characteristic part acquired by the designated characteristic part acquisition process among a plurality of the image information, wherein:

the focus position information acquisition process acquires a position, relating to the image information including the designated characteristic part extracted by the characteristic image detection process, as the focus position information, and the focus position information acquisition process causes a position indicated by the focus position information to be displayed on the diagram displayed by the position display process.

25. The image filing method for a capsule endoscope according to claim 24, wherein the position display process displays a trajectory path of the capsule endoscope in one or more luminal organs in the subject body while displaying the average locations of one or more internal organs in the subject body as a background of the trajectory path.

26. The image filing method for a capsule endoscope according to claim 24, wherein the progress information display process superimposes and displays the display indicating the progress and the processing result of the image information processing process on the display of the position display process.

27. The image filing method for a capsule endoscope according to claim 24, further comprising an image information display process for displaying progress of processing of the image information processing process and image information corresponding to the processing of the image information processing process.

28. The image filing method for a capsule endoscope according to claim 27, wherein the image information display process displays the processing result of the image information processing process in a way such that the display is superimposed on the display of the image information.

29. The image filing method for a capsule endoscope according to claim 27, wherein the image information display process updates and displays the image information at a prescribed time interval.

30. The image filing method for a capsule endoscope according to claim 27, further comprising an instruction input process for receiving an instruction from a method-operator, wherein the image information processing process performs a control of the image information processing based on the input result of the instruction input process.

31. The image filing method for a capsule endoscope according to claim 30, wherein the control of the image information processing in the image information processing process based on the input result from the instruction input process is the end of the processing.

32. The image filing method for a capsule endoscope according to claim 30, wherein the control of the image information processing in the image information processing process based on the input result from the instruction input process is the suspension of the processing.

33. The image filing method for a capsule endoscope according to claim 30, wherein the control of the image information processing in the image information processing process based on the input result from the instruction input process is the resumption of the processing.

34. The image filing method for a capsule endoscope according to claim 30, wherein the control of the image information processing in the image information processing process based on the input result from the instruction input process is the change in the image information to be processed.

35. A non-transitory recording medium recording an image filing processing program for a capsule endoscope for causing a computer to perform processing of successive image data captured in succession by a capsule endoscope moving in a subject body at a prescribed time interval, wherein the image filing processing program for a capsule endoscope, being executed by the computer, causes the computer to perform:
  focus position information acquisition processing for acquiring an arbitrary position from one or more of position information relating to the position in the subject body where the successive image data is acquired as focus position information;
  image information acquisition processing for acquiring image information corresponding to the position designated as the focus position information from the successive image data;
  storage processing for correlating and storing the image information and the position information;
  position display processing for displaying one or more of position information in the subject body as a diagram in at least two dimensions which is schematization of a luminal organ and which includes a body outline and a luminal organ outline, based on the position information stored by the storage processing;
  image information processing for applying a prescribed processing to the image information acquired by the image information acquisition processing;
  progress information display processing for superimposing and displaying the position of the focus position information acquired by the focus position information acquisition processing on the diagram displayed by the position display process, and for indicating the progress of processing by the image information processing by changing display of the focus position information on the diagram;
  a designated characteristic part acquisition processing for acquiring image information including a designated characteristic part based on information that is unique to the designated characteristic part; and
  a characteristic image detection processing for extracting the image information including the designated characteristic part acquired by the designated characteristic part acquisition processing among a plurality of the image information,
wherein:
  the focus position information acquisition processing acquires a position, relating to the image information including the designated characteristic part extracted by the characteristic image detection processing, as the focus position information, and
  the focus position information acquisition processing causes a position indicated by the focus position information to be displayed on the diagram displayed by the position display processing.

36. The recording medium according to claim 35, causing the computer to further perform the position display processing for displaying a trajectory path of the capsule endoscope in one or more luminal organs in the subject body while displaying the average locations of one or more internal organs in the subject body as a background of the trajectory path.

37. The recording medium according to claim 35, causing a computer to further perform the progress information display processing for superimposing and displaying the display indicating the progress and the processing result by the image information processing process on the display of the position display process.

38. The recording medium according to claim 35, wherein the image filing processing program for a capsule endoscope, by being executed by the computer, causes the computer to further perform an image information display processing for displaying progress of processing of the image information processing process and image information corresponding to the processing of the image information processing process.

39. The recording medium according to claim 38, wherein the image information display processing displays the processing result of the image information processing process in a way such that the display is superimposed on the display of the image information.

40. The recording medium according to claim 38, causing the computer to further perform processing for updating and displaying the image information at a prescribed time interval.

41. The recording medium according to claim 35, wherein the image filing processing program for a capsule endoscope, being executed by the computer, causes the computer to further perform instruction input processing for receiving an instruction from outside the computer and wherein
  the image information processing process causes the computer to control the image information processing based on the input result of the instruction input processing.

42. The recording medium according to claim 41, wherein the control of the image information processing in the image information processing process based on the input result received by the instruction input processing is the end of the processing.

43. The recording medium according to claim 41, wherein the control of the image information processing in the image information processing process based on the input result received by the instruction input process is the suspension of the processing.

44. The recording medium according to claim 41, wherein the control of the image information processing in the image information processing process based on the input result received by the instruction input process is the resumption of the processing.

45. The recording medium according to claim 41, wherein the control of the image information processing in the image information processing process based on the input result received by the instruction input process is the change in the image information to be processed.

* * * * *